United States Patent [19]
Taylor et al.

[11] Patent Number: 5,967,979
[45] Date of Patent: Oct. 19, 1999

[54] METHOD AND APPARATUS FOR PHOTOGRAMMETRIC ASSESSMENT OF BIOLOGICAL TISSUE

[75] Inventors: Geoffrey L. Taylor; Grant D. Derksen, both of Winnipeg, Canada

[73] Assignee: Verg, Inc., Winnipeg, Canada

[21] Appl. No.: 08/557,348

[22] Filed: Nov. 14, 1995

[51] Int. Cl.⁶ .................................................. A61B 05/00
[52] U.S. Cl. ........................................ 600/407; 356/375
[58] Field of Search ................................. 128/653.1, 897, 128/920, 922; 356/375, 379, 384, 388, 390, 243; 606/130; 348/77, 135; 600/407

[56] References Cited

U.S. PATENT DOCUMENTS

| | | |
|---|---|---|
| 4,535,782 | 8/1985 | Zoltan . |
| 4,724,480 | 2/1988 | Hecker et al. . |
| 4,736,739 | 4/1988 | Flaton . |
| 4,996,994 | 3/1991 | Steinhauer et al. . |
| 5,319,550 | 6/1994 | Griffith . |
| 5,363,854 | 11/1994 | Martens et al. . |
| 5,396,331 | 3/1995 | Kitoh et al. . |
| 5,532,824 | 7/1996 | Harvey et al. . |
| 5,603,318 | 2/1997 | Heilbrun et al. . |

FOREIGN PATENT DOCUMENTS

| | | |
|---|---|---|
| 1584405 | 2/1981 | European Pat. Off. . |
| 0119660 | 9/1984 | European Pat. Off. . |
| 0355221 | 2/1990 | European Pat. Off. . |
| 2642841 | 3/1978 | Germany . |
| 3420588 | 12/1984 | Germany . |
| 41 20 074 | 1/1992 | Germany . |

*Primary Examiner*—Marvin M. Lateef
*Assistant Examiner*—Shawna J Shaw
*Attorney, Agent, or Firm*—William L. Chapin

[57] ABSTRACT

A remote wound assessment method and apparatus includes forming an oblique image of a wound and a target plate containing a rectangle and placed near the wound. Using a novel method of determining vanishing points where photographic images of parallel lines on the target object intersect, coordinate transformations are calculated which map the oblique image of the rectangle into a normal image thereof. Using the same coordinate transformations, an oblique image of a wound adjacent to the target plate is mapped into a normal view thereof, allowing precise measurement of wound features. By forming two separate images of a wound and target plate at two different oblique inclinations, three dimensional features of a wound may be measured.

21 Claims, 21 Drawing Sheets

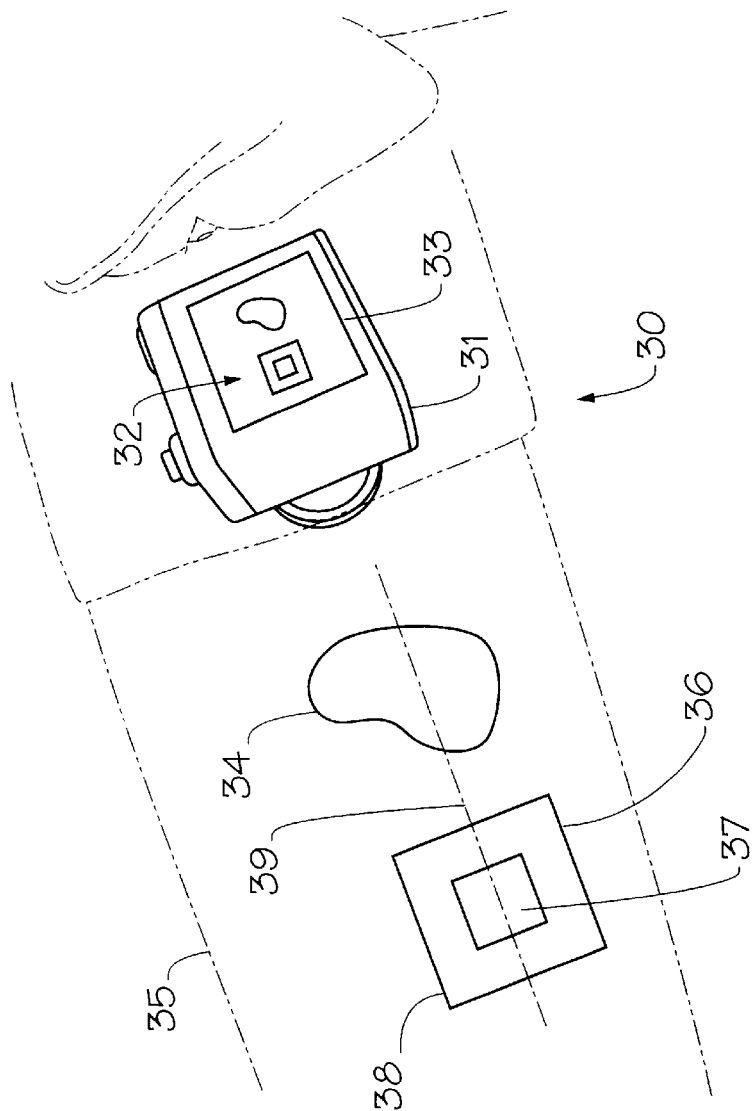
FIG. 2
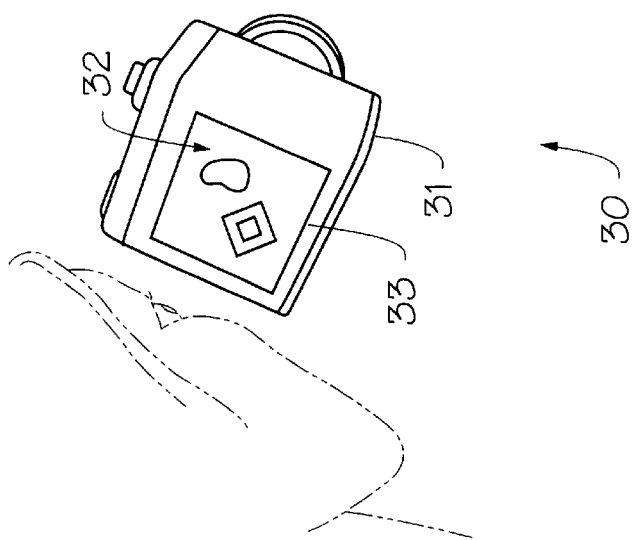

Small open wound: Area = 1.41 cm²
Large open wound: Area = 38.6 cm²
Figure 11: Image as seen in the picture (Angle view).
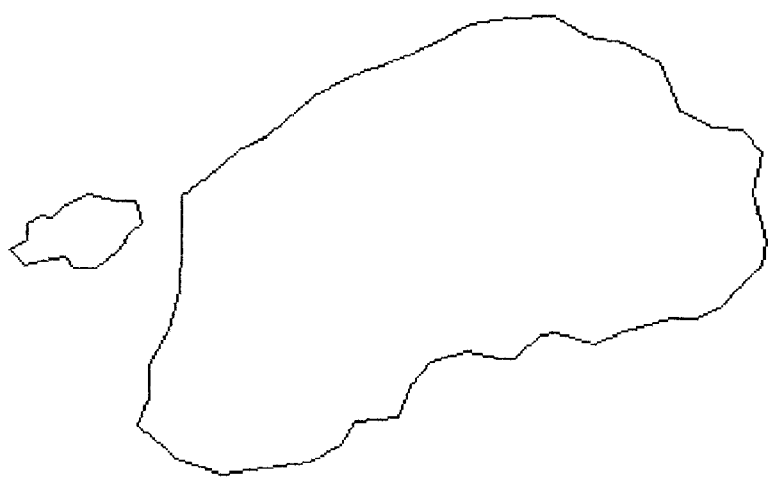
Figure 12: Image drawn to correct scale (1:1) as viewd 90° to wound.

Small open wound: Area = 0.50 cm²
Large open wound: Area = 31.8 cm²
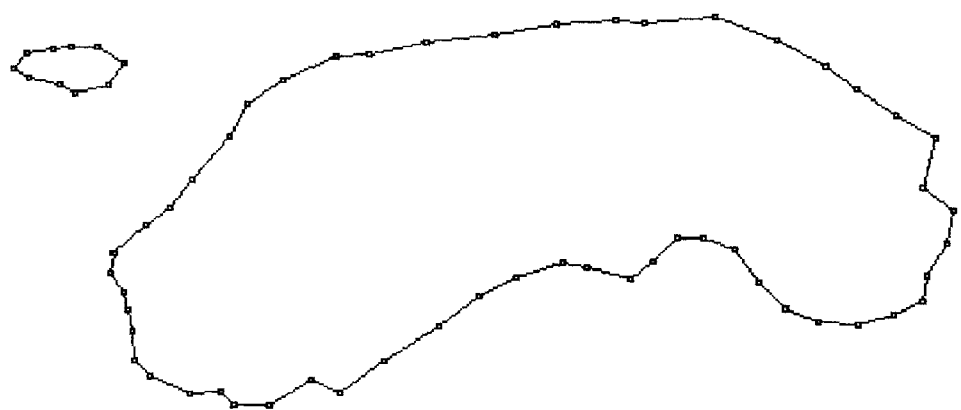
Figure 14: Image as seen in the picture (Angle view).
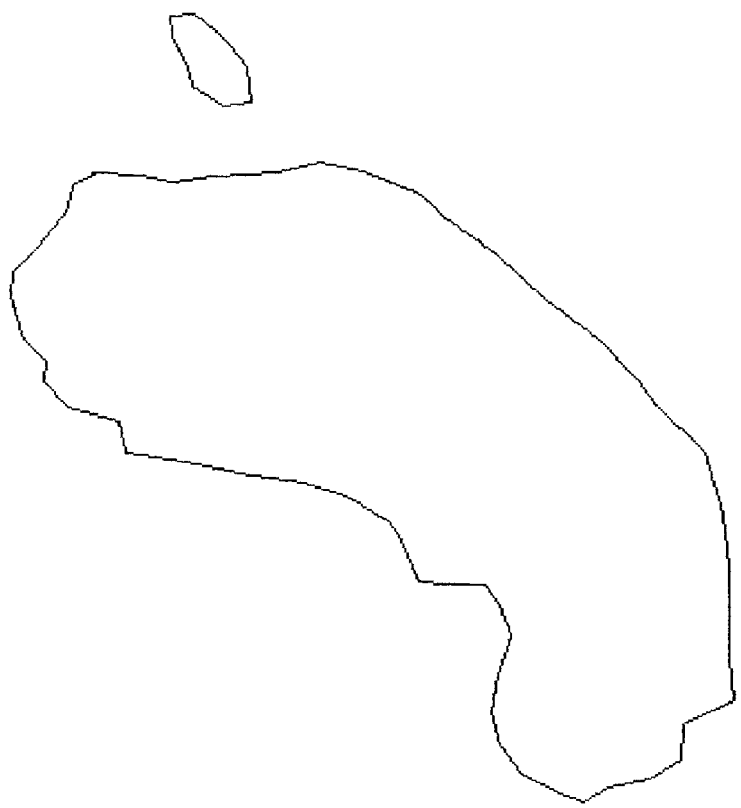
Figure 15: Image drawn to correct scale (1:1) as viewd 90° to wound.

Small open wound: Area = 0.50 cm²
Large open wound: Area = 34.5 cm²
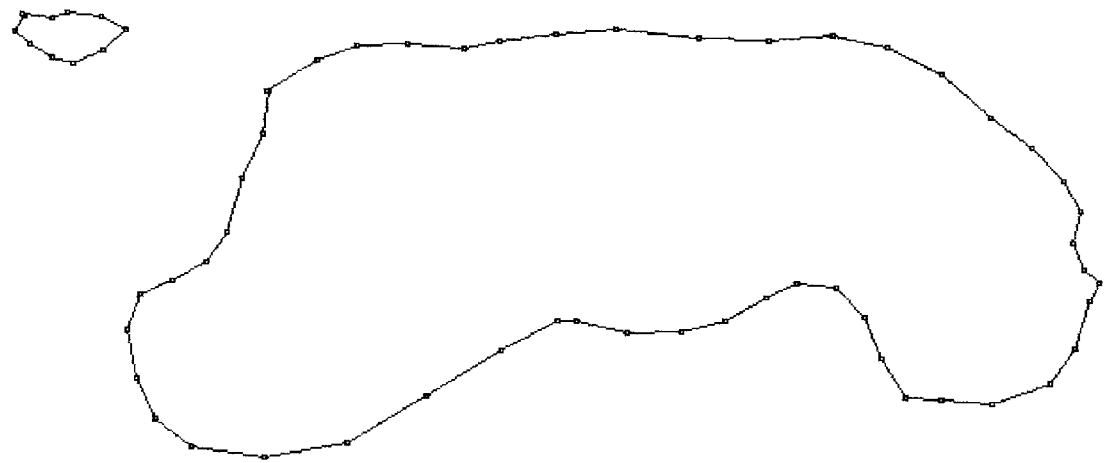
Figure 17: Image as seen in the picture (Angle view).
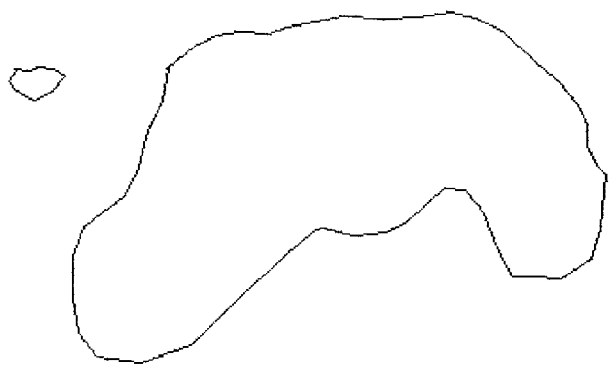
Figure 18: Image drawn to correct scale (1:1) as viewd 90° to wound.

Patient 5    Vascular insufficiency    Right leg ulcer

Grafted wound: Area = 38.5 cm²
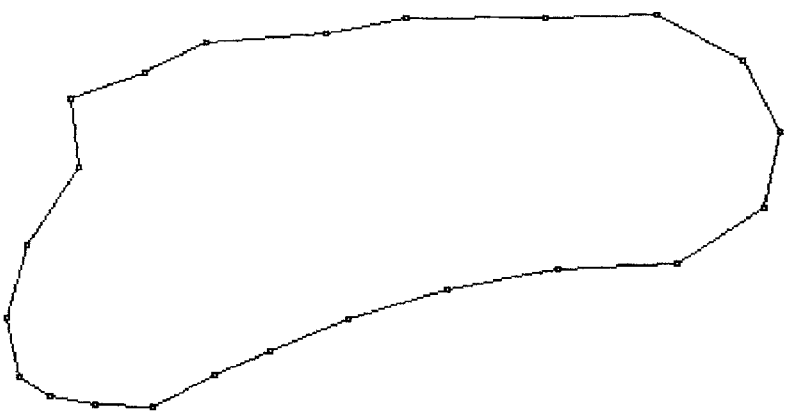
Figure 20: Image as seen in the picture (Angle view).
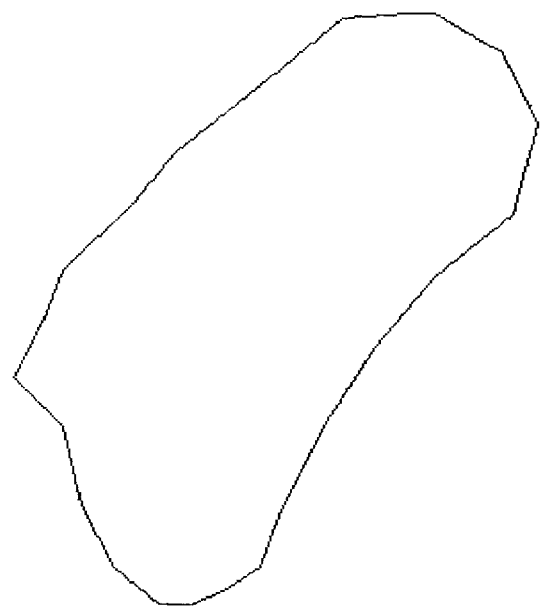
Figure 21: Image drawn to correct scale (1:1) as viewed 90° to wound.

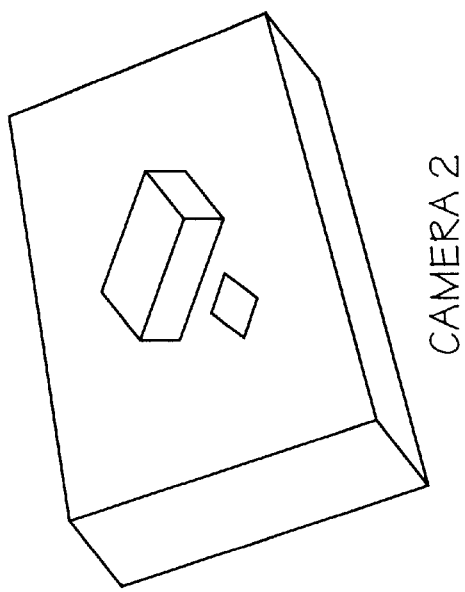
FIG. 23C CAMERA 2
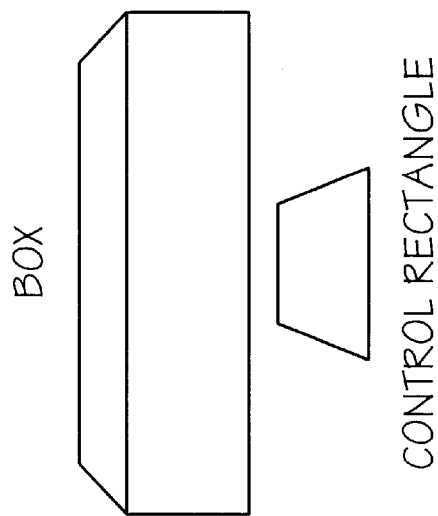
FIG. 23B
BOX
CONTROL RECTANGLE
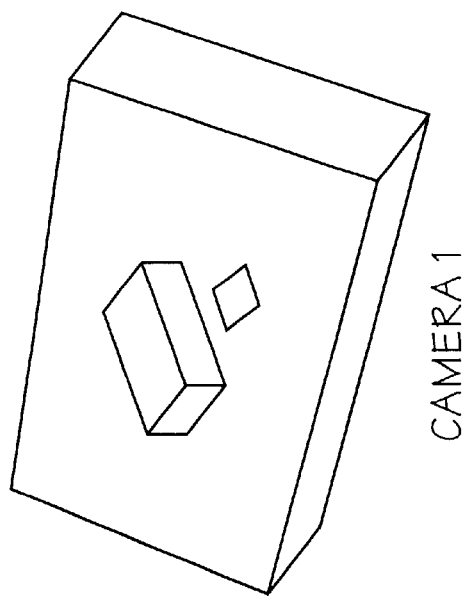
FIG. 23A CAMERA 1

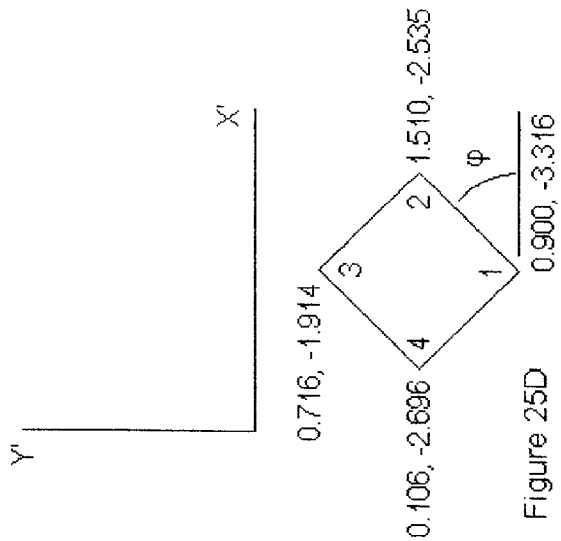
Figure 25D
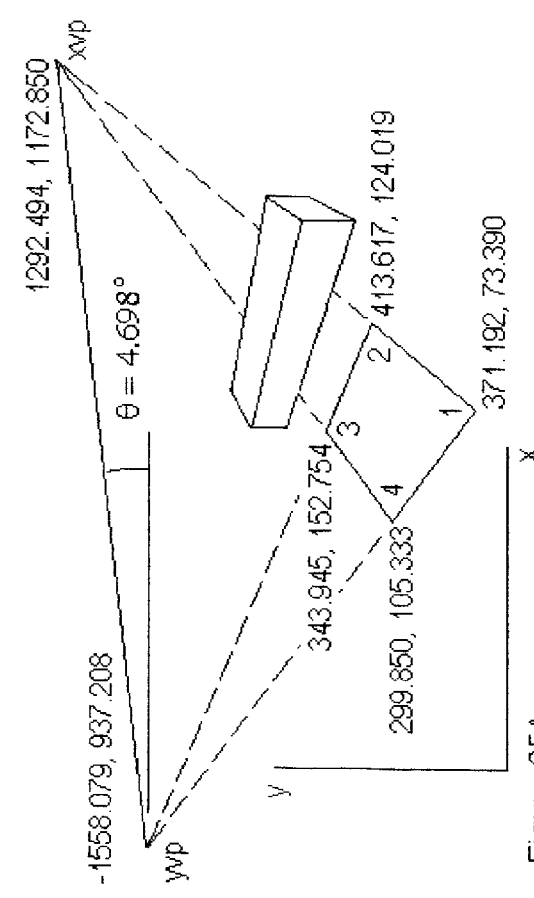
Figure 25A
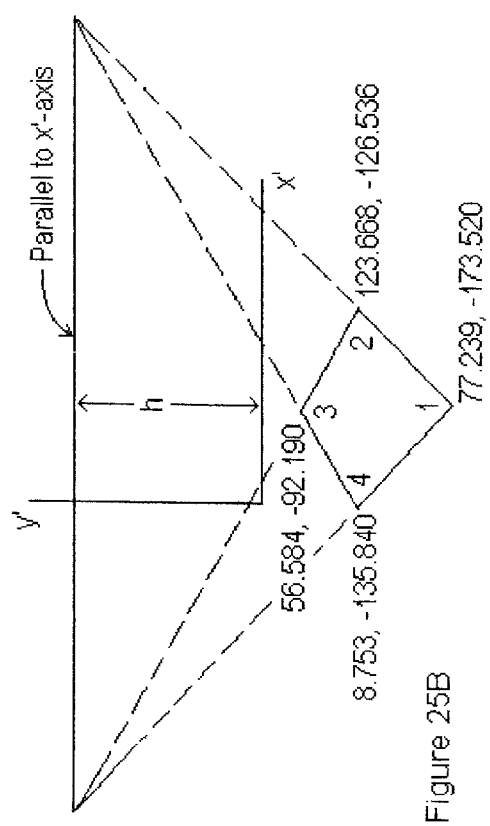
Figure 25B
Figure 25C

METHOD AND APPARATUS FOR PHOTOGRAMMETRIC ASSESSMENT OF BIOLOGICAL TISSUE

BACKGROUND OF THE INVENTION

A. Field of the Invention

The present invention relates to methods and apparatus for visually assessing the vitality of biological tissue. More particularly, the invention relates to methods and apparatus for remote photogrammetric assessment of the extent of wound damage to external tissues of a human or animal.

B. Description of Background Art

Treatment of external wounds to the bodies of humans and animals usually includes visual evaluations of the healing process by a medical doctor, veterinarian, nurse or clinical specialist. Such evaluations are necessary to determine whether the wound treatment regimen is successful in reducing the volume or damage to necrotic tissue, indicating a satisfactory rate of healing of the wound.

The expertise of experienced doctors or clinicians in visually assessing changes in color, texture or area size of damaged biological tissue is an important asset in determining the effectiveness of medical procedures used to treat wounds. However, a problem exists in measuring the size of wounds, to determine whether the area of damaged biological tissue is increasing or decreasing. Such quantitative assessments are particularly important in monitoring the growth rate of wounds infected by gangrene or "flesh-eating" bacteria, since the rapid unchecked growth of these infections can necessitate amputation, or result in death.

A number of devices have been disclosed that relate generally to the field of assisting in visual evaluation of human body parts, some of which utilize optical means. These include the following U.S. Pat. Nos.:

Kawahara, 3,817,635, Jun. 18, 1974, Device For Measuring The Actual Dimension Of An Object At The Forward End Portion Of An Endoscope:

Discloses a device for measuring the actual dimension of an object in the field of view of an endoscope, the forward end portion of which is adapted to be inserted into a hollow portion of a living body or the like for the inspection thereof. The endoscope is provided with a fixed focal length objective lens system, a differential mechanism, and a sizing means along with adjusting means for the objective lens system, and a distance measuring means. One sizing means disclosed comprises a caliper having measured spaced pointers. A second sizing means disclosed comprises a pair of blades pivotally mounted in symmetrical relation to each other, the blades provided with cut out portions adapted for size measurement. A third sizing means disclosed comprises an iris diaphragm. The actual size of an object appearing in the field of view is measured directly by differentially coupling the differential mechanism with the sizing means and either the adjusting means for the objective lens system, or the distance measuring means for measuring the size of the object appearing in the field of view. An indicating means coupled with the differential mechanism indicates directly the actual dimension of the object regardless of the variation in the distance between the object and the forward end portion of the endoscope.

Mizumoto, 4,278,077, Jul. 14, 1981, Medical Camera System:

Discloses a capsule-shaped miniature camera comprising at least one permanent magnet, an induction coil, a lamp serially connected to the induction coil and a shutter device. The induction coil induces an electromotive force when a magnetic field generated by electromagnets outside the camera acts on it. The electromotive force turns on the lamp and drives the shutter device.

Landwehr, 4,370,039, Jan. 25, 1983, Method and Apparatus For Photographically Measuring An Object:

Discloses a method in which a composite photographic picture is generated through double-exposure, whereby the object, as for instance a person, is photographed on one half of the picture whereas a grid pattern is photographed on the other half; for the second exposure, person and grid pattern change position. In each instance of exposure, a line pattern is projected onto the object under utilization of one movable or two fixed, overhung projectors. Equipment is enclosed, permitting easy change of scenery.

Zoltan, 4,535,782, Aug. 20, 1985, Method For Determining Wound Volume:

Discloses a non-contacting volume determination method for use on wounds, in which a known pattern of lines optically projected onto the volume to be determined. The image of the projection viewed from an angle other than the projection, axis, along with the image of a reference volume located near the volume to be determined, are used to accurately determine the unknown volume.

Hallous, 4,564,295, Jan. 14, 1986, Apparatus And Method For Projection Moire Topography:

Discloses an apparatus and method for obtaining an improved moire fringe pattern image of an object. A beam of incoherent light is projected at the object. A grating is disposed in the path of the beam projected at the object, this grating being referred to as a projection grating. Means are provided for focusing the beam reflected from the object to obtain an image at an image plane. This movable grating is referred to as a reference grating. Means are provided for recording the image at the image plane, the recording means being, for example, a photographic or video camera. In accordance with an important feature of the invention, means are provided for moving the projection grating and the reference grating in synchronism. In a preferred embodiment, the projection and reference gratings are mounted in spaced relation in a movable member, and the synchronized motion of the gratings is implemented by moving the member. In a form of the disclosure, a double-projection set-up is used wherein two projection beams are directed at the object through first and second movable projection gratings, respectively. In this embodiment, the first and second projection gratings are moved in synchronism with the reference grating. This is preferably achieved by mounting the three gratings in appropriate spaced relationship in a common member, and moving the member.

Gormley, 4,569,358, Feb. 11, 1986, Optical Micrometry Of Skin Surfaces:

Discloses an apparatus and method for measuring changes in the topology of a skin surface in which a series of casts are taken of the skin surface, using an elastomeric material such as silicone rubber in a liquid state which is later polymerized, the casts being taken of a skin surface over a period of time and then measured by means of an automatically focusing microscope to produce a quantitative model of the changes in the topology of the surface.

Landwehr, 4,786,925, Nov. 22, 1988, Photographic Contour Measurement:

Discloses a method for measuring contours of a human body in which horizontal lines are projected onto a person from a plurality of overhead projectors, each projecting at a 45 degrees angle, all of the projectors have parallel optical axes, the person being photographed with the projected raster superimposed.

Steinhauer et al., 4,996,994, Mar. 5, 1991, Apparatus For Photogrammetrically Measuring The Human Head:

Discloses a process device for the photogrammetrical measurement of the human head, especially of the middle region of the face with the eye sockets, the nose, the cheek bones and the brows, which is comprised of a projector for projecting a pattern image onto the face and two cameras which can simultaneously take two pictures from two different directions of the face and head with the pattern image projected on it. The two cameras and the projector are supported by an apparatus carrier, which can be moved in a vertical direction relative to a base permanently connected in the device and in at least one horizontal direction. This minimum of one direction coincides with the optical axes of the cameras. The device will facilitate bringing both the projector and the cameras on the one hand and the human head on the other into the required relative position to one another as necessary to take the pictures.

Of the prior art references cited above, those most applicable to the problem of optically assessing external body parts include Landwehr, 4,370,039, which discloses a method and apparatus for measuring body contours that uses a projected grid pattern on the body, and a double photographic exposure, with the body in different positions for the two exposures, Zoltan, 4,535,782, which discloses a non-contacting volume determination method for use on wounds, in which a grid pattern is projected onto the wound, and the wound and pattern photographed, Hallous, 4,564,295, which discloses a method and apparatus for remotely measuring surface contours of an object that uses one or more grid patterns produced by projecting light through a grating onto the object surface, and a reference grating that produces a Moire pattern with light reflected off of the object, the patterns to be photographed, and Landwehr, 4,786,925, which discloses a method for remotely measuring body contours by projecting a grid pattern onto the body, and photographing the reflected pattern. Steinhauer et al. 4,996,994, discloses an apparatus for making photogrammetric measurements of the human head using two cameras photographing a grid pattern projected on the head.

None of the prior art references known to the present inventors is particularly well-suited to either qualitative or quantitative assessment of wound characteristics, because the projected grid patterns or Moire patterns used in prior art methods obscure certain wound features. Moreover, none of the prior art provides means for quantitatively establishing the color boundary of a wound. The present invention was conceived of to provide a method and apparatus for photogrammetric assessment of biological tissue that overcomes limitations of the prior art.

OBJECTS OF THE INVENTION

An object of the present invention is to provide a method and apparatus for photographically assessing areas of damaged biological tissue.

Another object of the invention is to provide a photogrammetric wound assessment method and apparatus that does not require physical contact with a wound.

Another object of the invention is to provide a photogrammetric wound assessment method and apparatus which requires minimal or no contact with a patient's body.

Another object of the invention is to provide a photogrammetric wound assessment method and apparatus that provides repeatably quantifiable photographic views of a wound, in spite of varying locations of an optical image forming device such as a camera employed to form the views.

Another object of the invention is to provide a photogrammetric wound assessment method and apparatus that provides means for remotely and accurately measuring the area of a wound.

Another object of the invention is to provide a photogrammetric method and apparatus for wound assessment that may optionally provide a three dimensional image and measurements of wound depth in addition to wound area.

Another object of the invention is to provide a photogrammetric method and apparatus for wound assessment that provides means for transforming an oblique image of a wound formed by a camera having its line of sight inclined from a normal to a wound surface, to a normal image.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described in this specification are merely illustrative of the preferred embodiment. Accordingly, we do not intend that the scope of our exclusive rights and privileges in the invention be limited to details of the embodiments described. We do intend that equivalents, adaptations and modifications of the invention reasonably inferable from the description contained herein be included within the scope of the invention as defined by the appended claims.

SUMMARY OF THE INVENTION

Briefly stated, the present invention comprehends a method and apparatus for assessing the condition of biological tissue, particularly tissue which has been damaged by a wound, by remote optical means. According to the present invention, an optical imaging apparatus such as a still or video camera is used to photograph, at an oblique, arbitrary angle, a wound and target plate located physically near to the wound. The target plate contains at least one pair of lines that intersect at a known angle, and preferably contains two pairs of parallel lines that are mutually perpendicular, forming a rectangle. When photographed at an arbitrary oblique angle, the image of the target rectangle is in general a quadrilateral.

The method of the present invention includes locating on the photograph intersection points of lines on the target plate, either manually or, preferably, using a combination of image search algorithms and contrast edge discerning techniques. Using a novel method of determining a pair of vanishing points where photographic images of lines that are parallel in the real world intersect, coordinate transformations are calculated which map the photographic image into its real-world shape. These coordinate transformations are then used to map the intersecting lines of a quadrilateral image into an image normal to the plane of the target plate, thus mapping the quadrilateral image into the rectangular "real world" shape of the target plate. Using the same coordinate transformations, the oblique image of an adjacent wound is mapped into a normal view thereof. Measurement of the mapped image of the target plate allows precise two-dimensional measurements of the wound features, such as its perimeter, thereby permitting precise repeatable, remote measurement of the wound size and other characteristics.

In a variation of the method of the present invention that permits three-dimensional measurements of features such as wound depth, two separate photographs of a wound are made at two different oblique inclinations of the camera's focal axis with respect to the wound. Preferably, the two viewing angles are separated by about 45°. Mathematically combining two-dimensional coordinates of the two photographs thus obtained permits locating the Z-axis or depth coordinates of wound features, as well as their X-Y coordinates in the plane of the wound.

BRIEF DESCRIPTION OF THE DRAWINGS

FIG. 2 is a view similar to FIG. 1, but showing the imaging acquisition apparatus therein located at two separate oblique viewing positions relative to a wound, thereby providing three-dimensional photogrammetric wound data.

FIG. 11 is a planar image of the damaged tissue and target plate shown in FIG. 10, as imaged at an arbitrary, possibly oblique angle by the image forming apparatus shown in FIG. 1.

FIG. 12 is a re-oriented planar image of the damaged tissue and target plate similar to that of FIG. 11, but showing the damaged tissue and target plate viewed normally thereto, the re-orientation being performed by the method and apparatus of the present invention.

FIG. 14 is a planar view similar to that of FIG. 9, but taken at the same date as FIG. 13.

FIG. 15 is a re-oriented planar view similar to that of FIG. 12, but taken the same date as FIG. 13.

FIG. 17 is a planar view similar to that of FIG. 14, but taken at the same date as FIG. 16.

FIG. 18 is a re-oriented planar view similar to that of FIG. 15, but taken at the same date as FIG. 16.

FIG. 20 is a planar view similar to that of FIG. 17, but taken at the same date as FIG. 19.

FIG. 21 is a re-oriented view similar to that of FIG. 18, but taken at the same date as FIG. 19.

FIGS. 23A–23C are partly schematic views showing the geometric relationship between camera views, control rectangle and a box representing a limb being viewed by the method of the present invention, in which FIG. 23A is a left-hand camera view, FIG. 23B is a front perspective view, and FIG. 23C is a right-hand camera view.

FIGS. 25A–25D are schematic views illustrating object calculations for the right-hand images of FIGS. 23C and 24B, in which FIG. 25A shows calculations of vanishing points, point ordering, and rotation angle, FIG. 25B illustrates calculations of distance from focal center to horizon line, FIG. 25C illustrates transformation of an oblique view of a control rectangle to a normal view thereof, and FIG. 25D illustrates tranformation calculations of the yaw angle of the control rectangle. FIGS. 26A–26D are schematic views illustrating object size calculations for the left-hand image of FIGS. 23A and 24A, in which FIG. 26A shows calculations of vanishing points, point ordering and rotation angle, FIG. 26B illustrates calculation of distance from focal center to horizon thereof, and FIG. 26D illustrates calculation of the yaw angle of the control rectangle.

DESCRIPTION OF THE PREFERRED EMBODIMENTS

FIGS. 1–26 illustrate photogrammetric apparatus, articles and methods according to the invention for assessing conditions of biological tissues, such as wounds in humans or animals.

Figure 1:
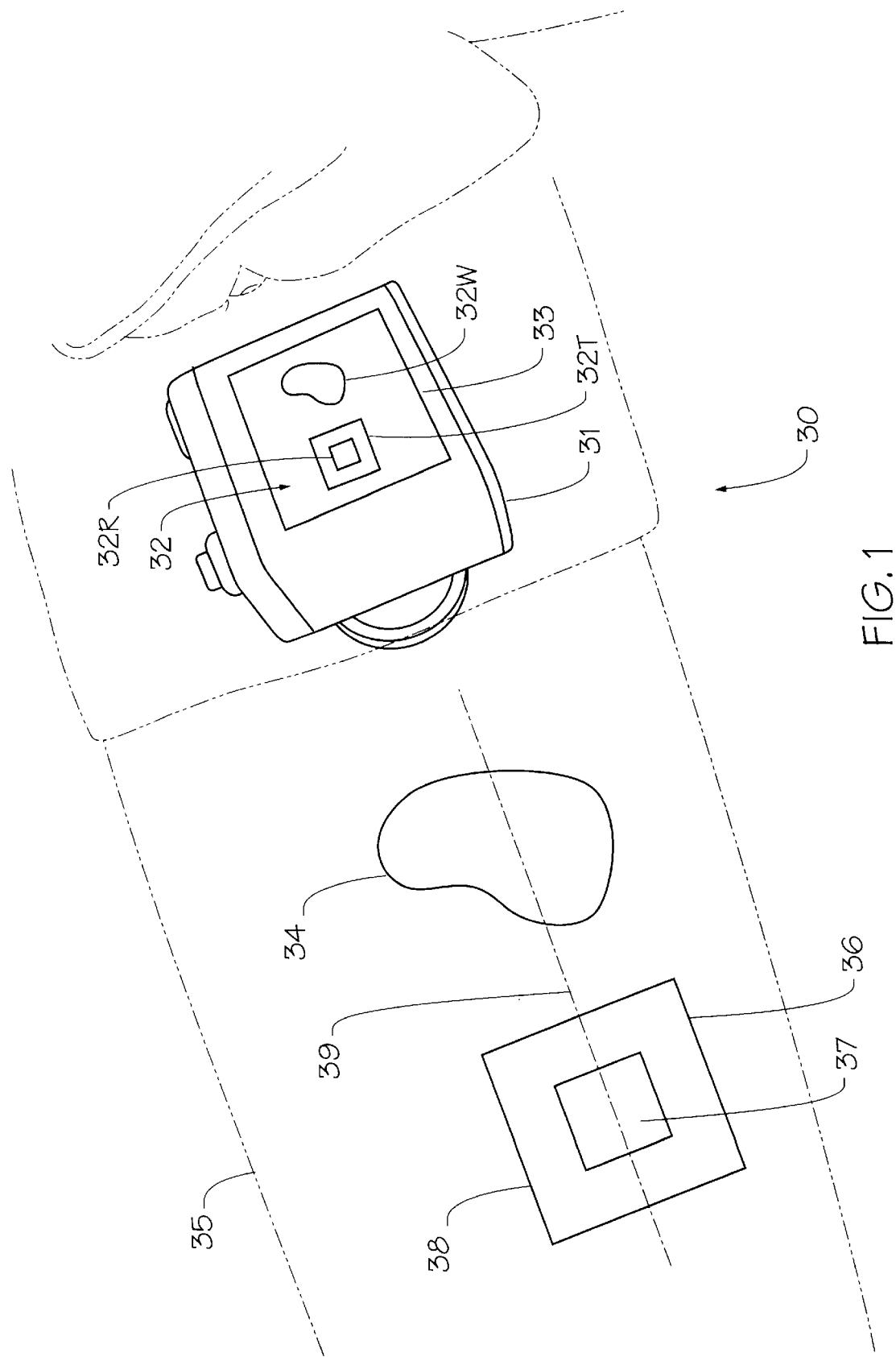
FIG. 1 is a partially diagrammatic view of a two-dimensional wound image acquisition apparatus and method according to the present invention.

Referring first to FIG. 1, a method of acquiring a visual image of biological tissue using an apparatus and article according to the present invention is shown. As will be made clear later in the description of the invention, visual images acquired as shown in FIG. 1 are processed by methods according to the present invention to quantify various parameters of tissues imaged.

As shown in FIG. 1, a biological tissue image acquisition apparatus 30 according to the present invention includes a visual imaging device 31, which may be a still photographic film camera such as a 35 mm camera, film motion picture camera, video camera, or digital still camera. As shown in FIG. 1, camera 31 is used to form an image 32 at the focal plane 33 of the camera. In the example of FIG. 1, biological tissue consisting of a wound 34 on the limb 35 of a patient forms an image 32W on the focal plane 33 of a camera 31. A target plate 36 adjacent to wound 34 also forms an image 32T, on the camera focal plane, which, with wound image 32W comprises a composite image 32.

According to the present invention, the image acquisition method and apparatus depicted in FIG. 1 includes a target plate 36 placed on or near the surface of limb 35, adjacent wound 34. As shown in FIG. 1, target plate 36 has a generally rectangular, preferably square shape, and has a rectangular central area 37 concentric with the perimeter 38 of the target plate. Central area 37 of target plate 36 is preferably of a different color or darkness than the remainder of the target plate. Thus, as shown in FIG. 1, central area 37 of target plate 36 may be white, while the remainder of the target plate may be black.

As shown in FIG. 1, target plate 36 is preferably placed on or near the surface of limb 35 at a location longitudinally displaced from wound 34, but in approximate longitudinal alignment with the wound. Preferably, the longitudinal axis of target plate 36 is aligned with a longitudinally disposed medial line 39 of wound 37. Also, target plate 36 is so positioned as to make the plane of the target plate approximately tangent to the upper surface of wound 34, at a longitudinal medial line 39 on the wound. As will be made clear in the ensuing description of the invention, precise alignment of target plate 36 relative to wound 34 and limb 35 is not required to obtain accurate photogrammetric measurements of the wound, according to the present invention. Preferably, however, the plane of the target plate is inclined no more than about ±10 degrees with respect to a tangent plane to the wound. This degree of alignment is readily accomplished by visual means alone.

Figure 7:
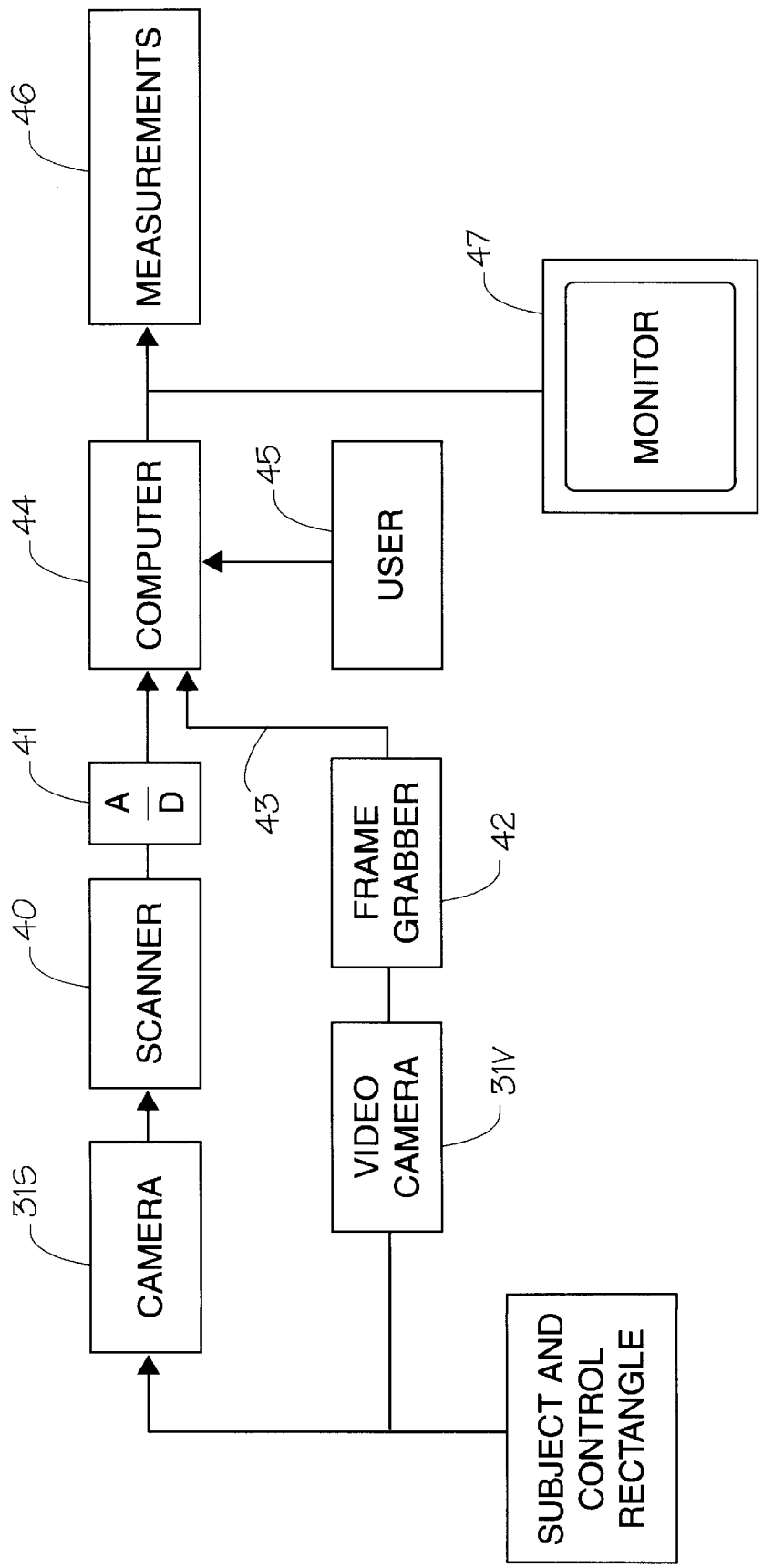
FIG. 7 is a block diagram of an apparatus used to make photogrammetric assessments of damaged biological tissue according to the present invention.
Figure 8:
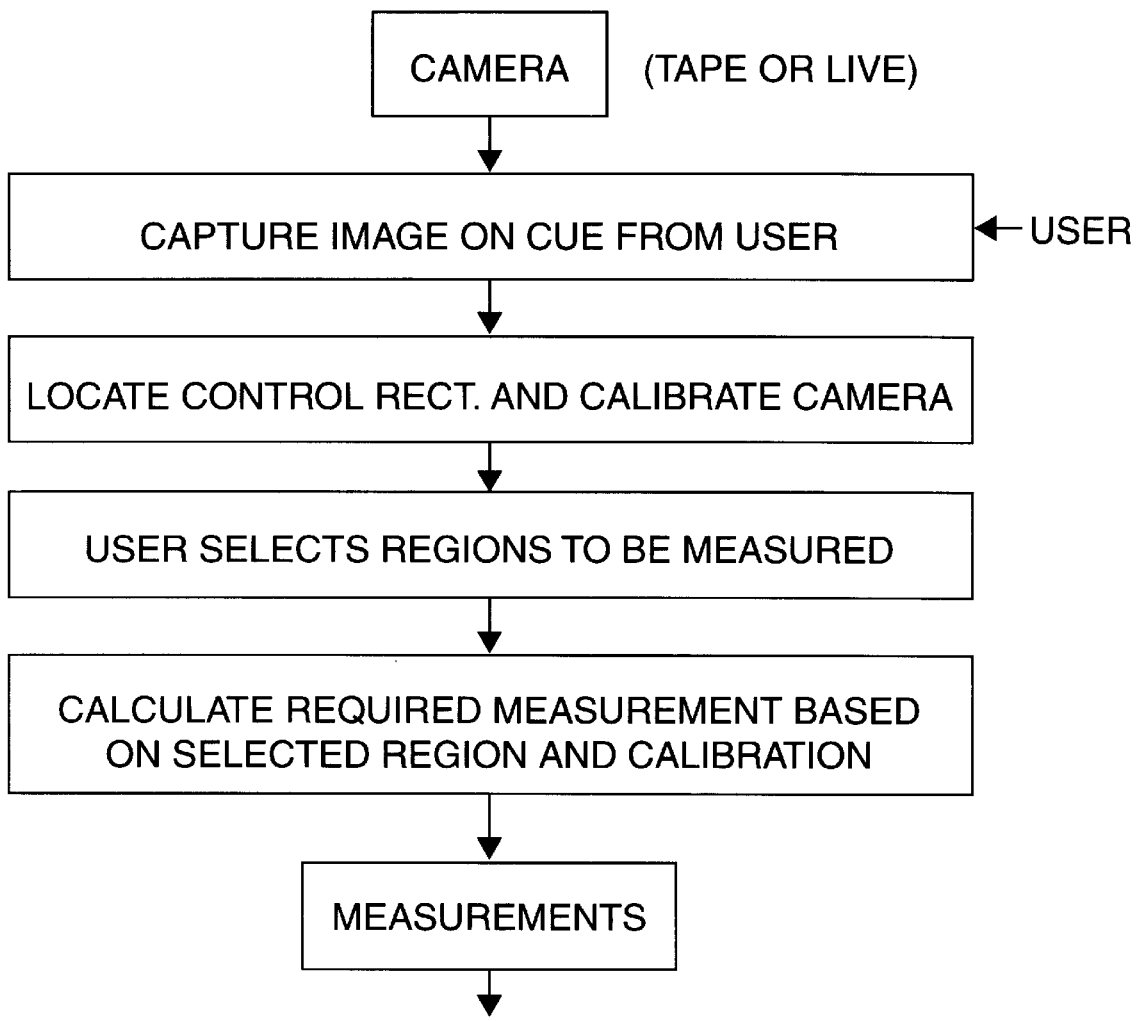
FIG. 8 is a simplified flow chart showing operation of the present invention.

After imaging device 31 has recorded a still or video frame containing an image frame 32 including an image 32W of a wound 34 and 32T of a target plate 36, the images are digitally processed according to the present invention, as shown in FIGS. 7 and 8. When imaging device 31 is a photographic still camera, employing photographic film, processing of image frame 32 requires that the exposed film be developed in a conventional fashion. The developed negative image may then be digitally processed according to the present invention. Alternatively, a positive print may be made of the negative, and digitally processed in a manner to be described below. Whether a film positive or negative image frame 32 is utilized, the method of the present invention preferably utilizes an optical scanner 40 and an analog-to-digital converter (A/D) 41 to convert the analog two-dimensional image into a digital image.

An X-Y scanner and A/D converter that was found satisfactory for the present invention is the Hewlett Packard brand Scan Jet TIOX scanner, which has a resolution of 600 DPI and a gray scale resolution of 24 bits.

As was previously stated, imaging device 31 may be a video camera rather than a still camera. In this case, optical scanner 40 and A/D converter 41 are replaced by a digital frame grabber 42 which converts optical images 32 into digital electronic images that are digitally processed according to the method and apparatus of the present invention. We have found that a suitable frame grabber for use in the present invention is a MRT brand video port model, having a resolution of 780×480 pixels, and a gray scale resolution of 24 bits. This device is manufactured by the MRT company, located in Norway.

Whether digitized image 32 is obtained by means of a still camera 31S or video camera 31V, the digitized image 43 is processed by novel methods according to the present invention, in a manner which will now be described.

As shown in FIG. 7, the photogrammetric assessment method according to the present invention utilizes a computer 44 operated by a user 45 to make measurements 46 of certain parameters of wound image 34. As will now be explained in detail, the method includes re-orienting images of wound 34 and target plate 36 formed at arbitrary, oblique inclinations of the optical axis of camera 31 to limb 35 into normal (perpendicular) views of the target plate and wound, thereby allowing repeatable, accurate measurements of wound features, such as wound area.

The method according to the present invention of reorienting or mapping an oblique camera view of wound 34 into a normal view, perpendicular to the wound, may be best understood with reference to FIGS. 3–7. Mapping or re-orienting an image of a wound 34 photographed at an "arbitrary" oblique angle includes the step of mapping an oblique view of a target rectangle 36, which oblique view is in general a quadrilateral, into a rectangle. Now target rectangle 36 is assumed to have been located in a plane tangent to the wound when the composite image 32 of the wound and target plate was originally formed, as shown in FIG. 1. Therefore, mapping or re-orienting the quadrilateral image into a rectangular image results in re-oriented, normal (perpendicular) "real world" views of the wound as well as the target rectangle. Also, since the size of the target rectangle is known, the dimensions of the normal image of the wound are of a known scale. These two factors permit accurate, repeatable remote measurements of wound dimensions such as the perimeter and area of the wound, independent of camera optical axis inclination relative to the wound, and independent of camera lens focal length and distance between the camera and the wound.

Figure 3:
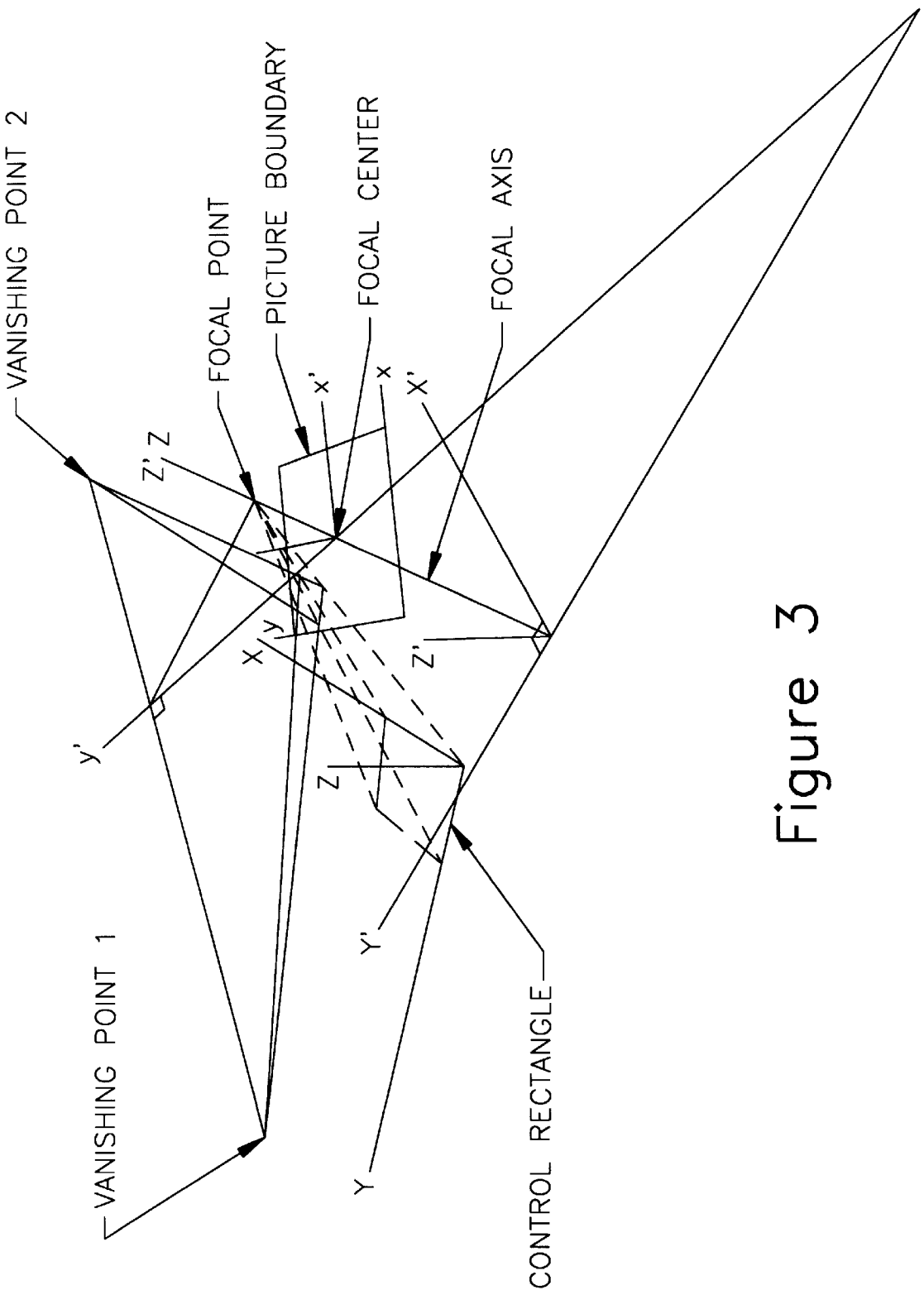
FIG. 3 is a perspective diagrammatic view showing the geometrical relationship between the plane of a wound image formed according to FIG. 1, and an imaging control plane constructed from the image of a target object located near the wound of FIG. 1.

The mapping or re-orientation method according to the present invention and referred to above is achieved by utilizing coordinate transformations which mathematically project the camera image into a "control plane" in which the target plate quadrilateral image is transformed into a rectangle having the same "real-world" scaled dimensions and angles as the actual target plate. This operation is shown in FIG. 3, which depicts a perspective view of the mapping geometry. The mapping step of the wound assessment method by photographic measurements (photogrammetric) according to the present invention may be best understood by reference to FIGS. 3–6.

Coordinate Systems

The photogrammetric wound assessment method according to the present invention preferably utilizes four coordinate systems, such as those shown in FIGS. 3–6.

In the coordinate systems of FIGS. 3–6, the focal point is defined as the point of convergence of all rays of light passing both through an oblique picture plane image and a re-oriented, normal image in the control plane.

The x,y,z coordinate system has its origin at the bottom left corner of the picture. The positive z axis is normal to the picture plane and directed towards the focal point, the positive y axis is parallel to the vertical edge of the picture and directed toward the top left corner of the picture. The x axis is normal to the yz plane.

Figure 5:
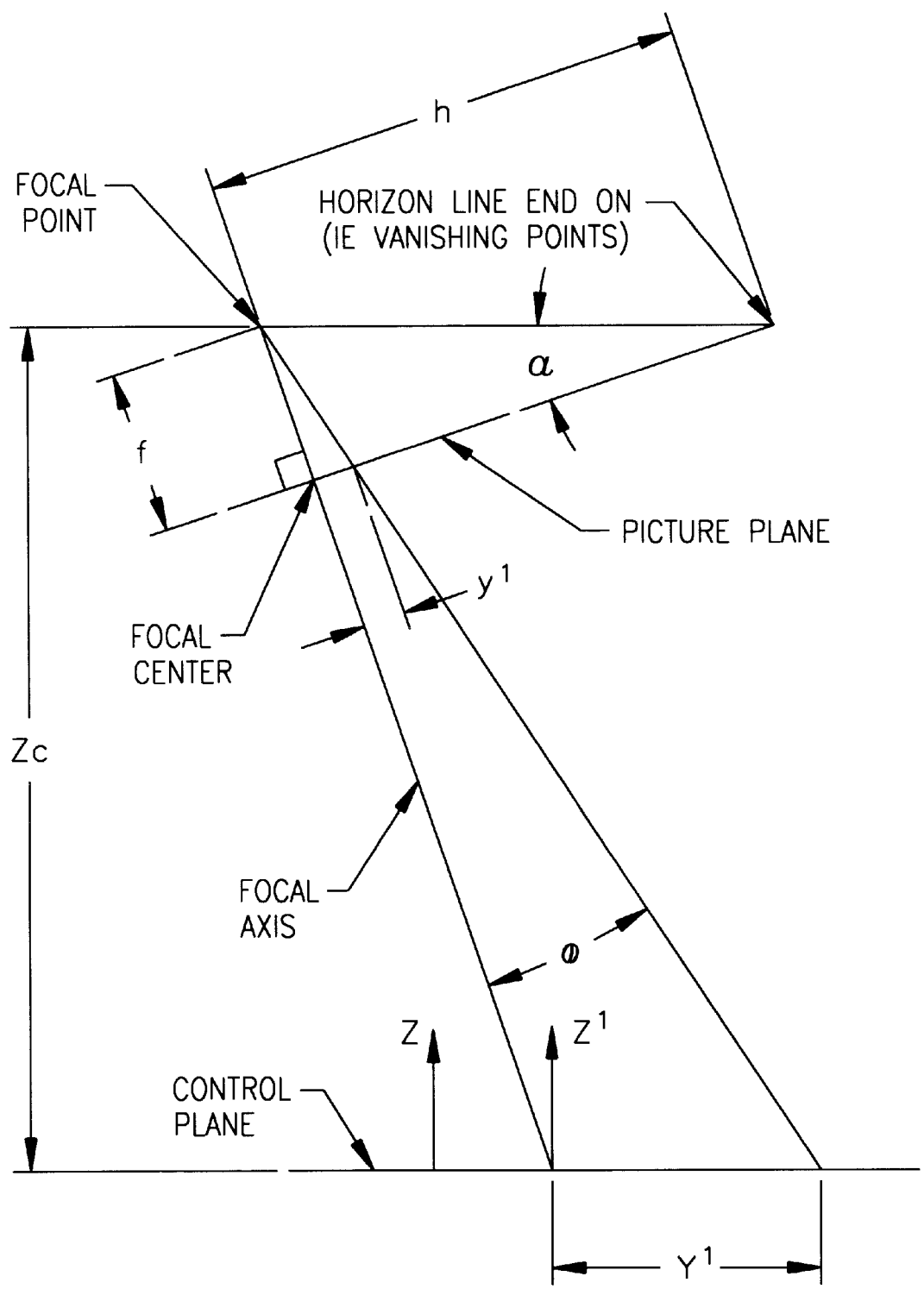
FIG. 5 is an orthogonal view of the coordinate system of FIG. 4, taken in the direction 5—5.
Figure 6:
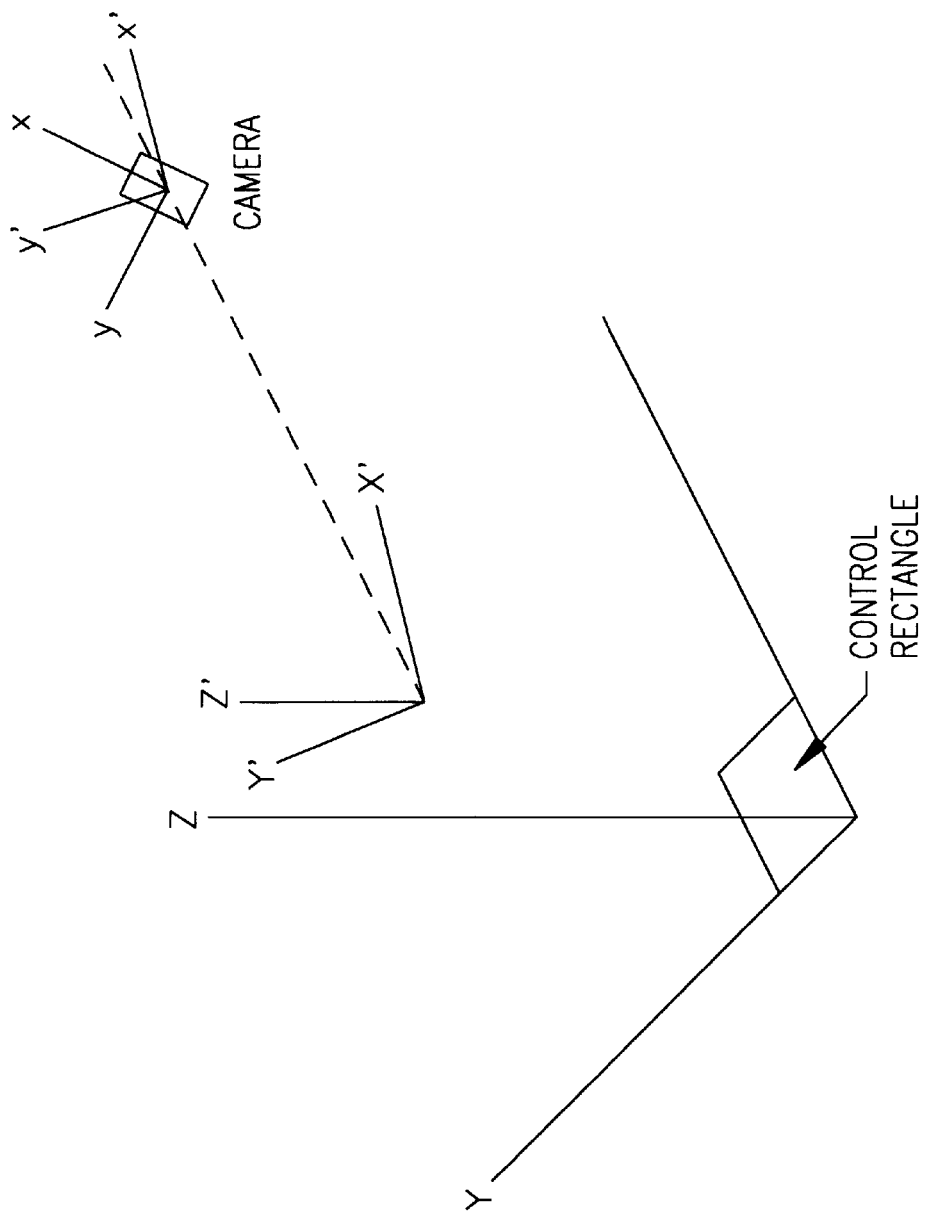
FIG. 6 is a perspective view of a coordinate system having an origin selected by an operator of the apparatus according to the present invention.

As shown in FIG. 5, the focal axis is the axis which is normal to the picture plane and passes through the focal point. The point where the focal axis intersects the picture plane is the focal center ($x_0$, $y_0$, 0).

Figure 4:
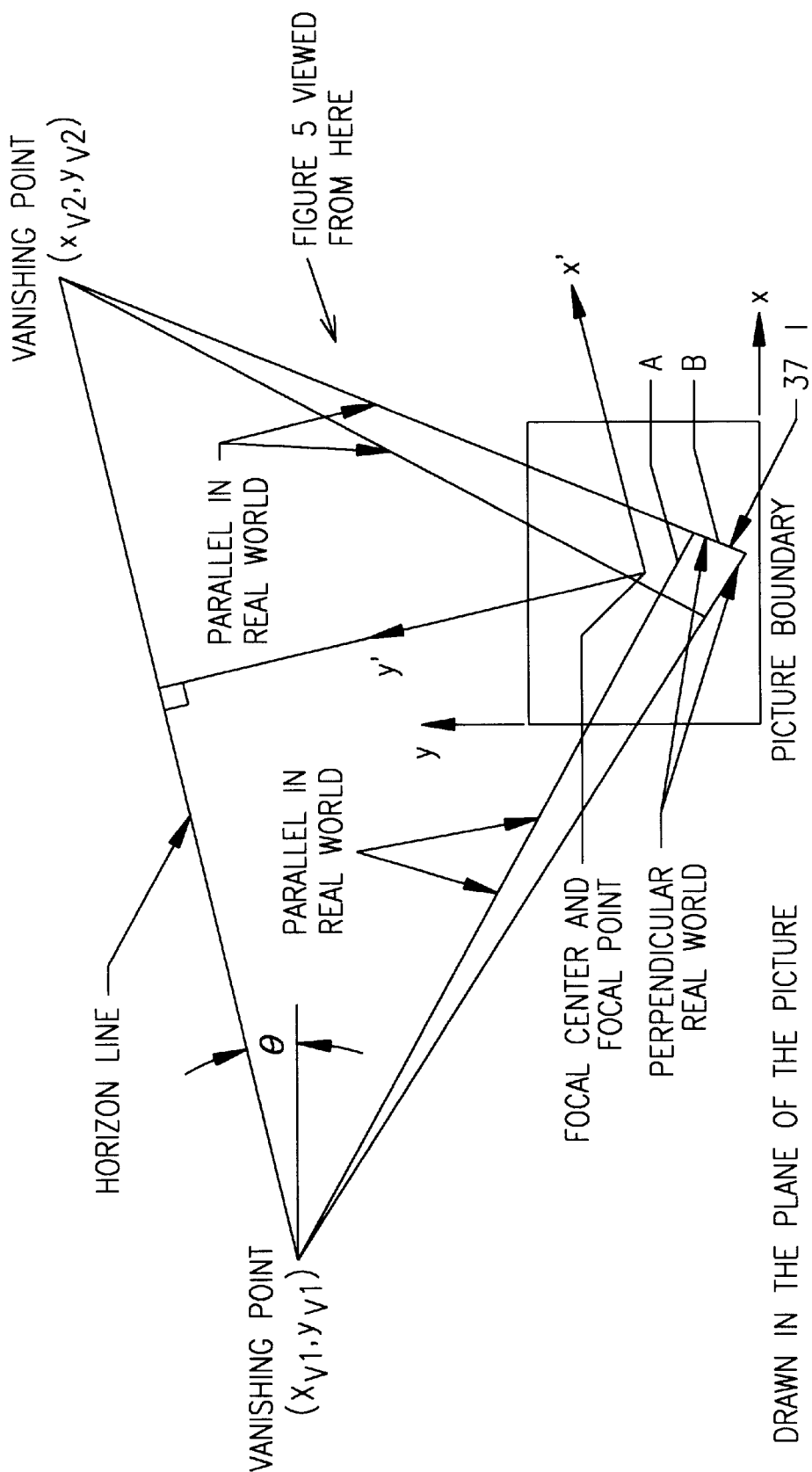
FIG. 4 is a diagrammatic view of a coordinate system based upon a perspective planar view of a picture image obtained with the apparatus shown in FIG. 1, with the image oriented parallel to the plane of the figure.

Referring now to FIG. 4, the x', y', z' coordinate system is defined by finding the objects in the picture that represent the real-world pairs of parallel, mutually perpendicular lines of the target plate. For each of the two pairs of parallel lines, their points of intersection are determined and called vanishing points with coordinates ($x_1$, $y_1$, 0) and ($x_2$, $y_2$, 0). The horizon line is defined as the line that passes through the two vanishing points.

As shown in FIG. 3, the x', y', z' coordinate system has its origin at the focal center. The positive z' axis is normal to the picture plane and directed toward the focal point, the positive y' axis is perpendicular to and directed at the horizon line and the x' axis is normal to the y'z' plane.

Referring still to FIG. 3, the X', Y', Z' coordinate system may be seen to have its origin at the point where the focal axis intersects the control plane. The positive Z' axis is normal to the control plane and directed toward the camera focal point, while the positive Y' axis is perpendicular to the line defined by the intersection of the picture plane and the control plane and is directed away from the camera. The X' axis is normal to the Y'Z' plane.

As shown in FIG. 3, the X, Y, Z coordinate system has its origin at a user selected point in the control plane. The positive Z axis is normal to the control plane and directed toward the camera focal point, while the positive Y axis is directed toward a second user selected point. The X axis is normal to the YZ plane.

Procedure For Calculating Camera Orientation From A Picture

Calculate the Vanishing Point's Coordinates

Referring now to FIG. 4, the vanishing points $V_1$ (X-axis) and $V_2$ (Y-axis) are determined by the intersection of the two sets of parallel lines of the target rectangle using the equations:

$$X_{xvp} = (B_2 \cdot C_1 - B_1 \cdot C_2)/(B_1 \cdot A_2 - B_2 \cdot A_1) \; V_1 \text{ Eqn.} \tag{1}$$

$$Y_{xvp} = -(C_1 + A_1 \cdot X_{xvp})/B_1 \tag{2}$$

$$X_{yvp} = (B_4 \cdot C_3 - B_3 \cdot C_4)/(B_3 \cdot A_4 - B_4 \cdot A_3) \; V_2 \tag{3}$$

$$Y_{yvp} = -(C_3 + A_3 \cdot X_{yvp})/B_3 \tag{4}$$

where $A_1$, $B_1$, $C_1$ and $A_2$, $B_2$, $C_2$ are the coefficients of one set of parallel lines and $A_3$, $B_3$, $C_3$ and $A_4$, $B_4$, $C_4$ are the coefficients of the other set of parallel lines.

Calculate the Rotation Angle, $\theta$

The rotation angle equals the angle between the x-axis and the vector running from the y-axis vanishing point (yvp) to the x-axis vanishing point (xvp).

$$\theta = \text{Tan}^{-1}((Y_{xvp} - Y_{yvp})/(X_{xvp} - X_{yvp})) \tag{5}$$

Convert x, y Coordinates to x', y' Coordinates:

Referring still to FIG. 4 and defining the angle between the positive x axis and the horizon line as the rotation angle $\theta$, then to transform a point in the x, y coordinates system to the x', y' coordinates system.

$$x' = (x - x_0) \cdot \cos \theta + (y - y_0) \cdot \sin \theta \tag{6}$$

$$y' = (y - y_0) \cdot \cos \theta - (x - x_0) \cdot \sin \theta \tag{7}$$

Calculate the Distance from the Focal Center to the Horizon Line, h:

$$h = y' \text{ of } v_1 \tag{8}$$

or $$h = y' \text{ of } v_2 \tag{9}$$

Calculate the Focal Length, f, in the Picture Coordinate System:

If $x'_1$, $y'_1$ and $x'_2$, $y'_2$ are the coordinates of the two end points of one of the known lengths (segment A of target rectangle) then let $$U_{12}, \text{ be defined as: } (x'_1/(h-y'_1) - x'_2/(h-y'_2))^2 \tag{10}$$

$$V_{12}, \text{ be defined as: } (y'_1/(h-y'_1) - y'_2/(h-y'_2))^2 \tag{11}$$

If $x'_3$, $y'_3$ and $x'_4$, $y'_4$ are the coordinates of the two end points of the other known length (segment B of target rectangle) then let $$U_{34}, \text{ be defined as: } (x'_3/(h-y'_3) - x'_4/(h-y'_4))^2 \tag{12}$$

$$V_{34}, \text{ be defined as: } (y'_3/(h-y'_3) - y'_4/(h-y'_4))^2 \tag{13}$$

If $D_{12}$ is the length of segment A and $D_{34}$ is the length of segment B in the camera coordinate system, then $$Z_c = ((f \cdot h \cdot D_{12})^2/(H^2 \cdot h^2 \cdot U_{12} + H^4 \cdot V_{12}))^{1/2} \tag{14}$$

And the focal length in the picture coordinate system is determined by:

$$f = h \cdot ((U_{12} - R \cdot U_{34})/(R \cdot V_{34} - V_{12}) - 1)^{1/2} \tag{15}$$

Calculate the Distance from the Camera to the Control Plane, Z in the Real World Coordinate System:

$$Z_c = ((f \cdot h \cdot D_{12})^2/H^2 \cdot h^2 \cdot U_{12} + H^4 \cdot V_{12}))^{1/2} \tag{16}$$

Where $H = (h^2 + f^2)^{1/2}$

Calculate the Pitch Angle, $\alpha$ in the Real World Coordinate System:

Referring now to FIG. 5, the pitch angle is defined as the angel between the picture plane and the control plane and is determined by:

$$\alpha = \text{Tan}(f/h) \tag{17}$$

Converting x', y' coordinates to X', Y' coordinates:

$$X' = M \cdot x'/(h - y') \text{ where } M = Z_c \cdot H/f \tag{18}$$

$$Y' = N \cdot y'/(h - y') \text{ where } N = Z_c \cdot H^2/(f \cdot h) \tag{19}$$

Calculate the Yaw Angle $\phi$:

The yaw angle $\phi$ is defined as the angle of rotation between the X', Y', Z' coordinate system and the X, Y, Z coordinate system. Calculate the X', Y' coordinates of two points in the picture and determine the equation of the line that passes through both points from the equation:

$$A \cdot X' + B \cdot Y' + C = 0 \tag{20}$$

where $A = Y'_2 - Y'_1$, $B = X'_1 - X'_2$ and $C = X'_2 \cdot Y'_1 - X'_1 \cdot Y'_2$ If the line's equation in X, Y, Z space is defined as:

$$D \cdot X' + E \cdot Y' + F = 0, \tag{21}$$

then the angle between the two lines and thus the yaw angle is:

$$\phi = \text{Tan}^{-1}((A \cdot E - D \cdot B)/(A \cdot D + B \cdot E)) \tag{22}$$

Converting X', Y' Coordinates to X, Y Coordinates:

$$X = (X' - X'_0) \cdot \cos \phi + (Y' - Y'_0) \cdot \sin \phi \tag{23}$$

$$Y = (Y' - Y'_0) \cdot \cos \phi - (X' - X'_0) \cdot \sin \phi \tag{24}$$

Note that the Z component is equal to the Z' component and is defined as 0.

Calculate the Camera Position (FIG. 6) $X_c Y_c$ in the Real World Coordinate System:

$$X'_c = 0 \tag{25}$$

$$Y'_c = -f \cdot Z_c/h \tag{26}$$

$$X_c = X'_0 \cdot \cos \phi + (Y' - Y'_0) \sin \phi \tag{27}$$

$$Y_c = (Y'_c - Y'_0) \cdot \cos \phi - X'_0 \cdot \sin \phi \tag{28}$$

3D Application: A variation of the photogrammetric method according to the present invention allows measurement of depth as well as surface dimensions of wound features. Thus, as shown in FIG. 2, two pictures may be taken from two separate oblique positions $(X_{-1}, Y_{-1}, Z_{-1})$ and $(X_{-2}, Y_{-2}, Z_{-2})$ viewing a limb 35, preferably separated by between about 15° and 165°. The three dimensional "3-D" coordinates of a point (Point A in FIG. 24, for example) visible in both pictures, can then be determined by triangulation, according to the following procedure. Procedure:

First, the X, Y Coordinates of the Point A as projected onto the control plane from the point of view of both pictures are located and identified as $(X_1, Y_1, 0)$ and $(X_2, Y_2, 0)$. Second, a line is constructed from focal point 1 to the projected point 1. Similarly, a line is constructed between focal point 2 and projected point 2. The coordinates of the Point A are the coordinates of the intersection of the two lines. Because of errors in calculations, the two lines may not intersect. The point where they come closest to each other would then be considered the coordinates of Point A.

Proofs

Proof for Equation 19:
Define Y' as a function of its projected point in the picture (x', y'). See FIG. 5.

$$Y'=Z_c \bullet (\tan(\alpha+\phi)-\tan\alpha)/ \quad (29)$$

$$Y'=Z_c \bullet ((\tan\alpha+\tan\phi)/(1-\tan\alpha\bullet\tan\phi)-\tan\alpha)) \quad (30)$$

Since $\tan\alpha=f/h$, $\tan\phi=y'/f$:  (31)

$$Y'=Z_c \bullet (f/h+y'+f)/(1-y'/h)-f/h) \quad (32)$$

$$Y'=Z_c \bullet ((f+y'\bullet h/f)/(h-y')-(f-f\bullet y'/h)/h-y')) \quad (33)$$

$$Y'=Z_c \bullet y' \bullet (h^2+f^2)/(h-y')\bullet f\bullet h \quad (34)$$

Define $H=(h^2+f^2)^{1/2}$  (35)

Define $N=Z_c \bullet H^2/(f\bullet h)$:  (36)

yielding equation 19

$$Y'(x', y')=N\bullet y'/(h-y') \quad (37)$$

Proof for Equation 18:
Define X' as a function of its projected point in the picture (x', y'):

$$X'/Z_c=x'/z \quad (38)$$

$$z=f\bullet\cos\alpha-y'\bullet\sin\alpha \quad (39)$$

Since $\cos\alpha=h/H$, $\sin\alpha=f/H$:  (40)

$$X'=Z_c \bullet H\bullet x'/((h-y')\bullet f) \quad (41)$$

Define $M=Z_c \bullet H/f$:  (42)

yielding equation 18

$$X'(x', y')=M\bullet x'/(h-y') \quad (43)$$

Camera Orientation From A Picture

Proof for Equation 16:
Define the height of the camera off the control plane, $Z_0$:

$$(X'_1-X'_2)^2+(Y'_1-Y'_2)^2=D_{12}^2 \quad (44)$$

$$(M\bullet x'_1/(h-y'_1)-M\bullet x'_2/(h-y'_2))^2+(N\bullet y'_1/(h-y'_1)-N\bullet Y'_2/(h-y'_2))^2=D_{12}^2 \quad (45)$$

$$M\bullet(x'_1/(h-y'_1)-x'_2/(h-y'_2))^2+N^2\bullet(y'_1/(h-y'_1)-y'_2/(h-y'_2))^2=D_{12}^2 \quad (46)$$

Define $U_{12}=(x'_1/(h-y'_1)-x'_2/(h-y'_2))^2$:  (47)

$$V_{12}=y'_1/(h-y'_1)-y'_2/(h-y'_2))^2 \quad (48)$$

$$M^2\bullet U_{12}+N^2\bullet V_{12}=D_{12} \quad (49)$$

Substituting for M and N:

$$(Z_c \bullet H/f)^2 * U_{12}+(Z_c \bullet H^2/(f\bullet h))^2 * V_{12}=D_{12} \quad (50)$$

Reducing:

$$(H^2 \bullet h^2 \bullet U_{12}+H^4 \bullet V_{12})/(f^2 \bullet h^2)=D_{12}/Z_c^2 \quad (51)$$

$$Z_c^2=(f\bullet h\bullet D_{12})^2/(H^2 \bullet h^2 \bullet U_{12}+H^4 \bullet V_{12}) \quad (52)$$

yielding equation 16

$$Z_c=((f\bullet h\bullet D_{12})^2/(H^2 \bullet h^2 \bullet U_{12}+H^4 \bullet V_{12}))^{1/2} \quad (53)$$

Proof for Equation 15:
Define focal-length f:
Equating the $Z_c^2$ equation for $D_{12}$ and $D_{34}$:

$$(f\bullet h\bullet D_{12})^2/(H^2 \bullet h^2 \bullet U_{12}+H^4 \bullet V_{12})=(f\bullet h\bullet D_{34})^2/(H^2 \bullet h^2 \bullet U_{34}+H^4 \bullet V_{34}) \quad (54)$$

Reducing:

$$(D_{12}^2/D_{34}^2)\bullet(H^2 \bullet h^2 \bullet U_{34}+H^4 \bullet V_{34})=H^2 \bullet h^2 \bullet U_{12}+H^4 \bullet V_{12} \quad (55)$$

Define $R=(D_{12}^2/D_{34}^2)$:
Substituting for H and reducing:

$$R\bullet(h^2 \bullet U_{34}+(h^2+f^2)\bullet V_{34})-h^2 \bullet U_{12}+(h^2+f^2)\bullet V_{12} \quad (56)$$

$$R\bullet(h^2 \bullet U_{34}+h^2 \bullet V_{34}+f^2 \bullet V_{34})=h^2 \bullet U_{12}+(h^2 \bullet V_{12}+f^2)\bullet V_{12} \quad (57)$$

$$f^2 \bullet (R\bullet V_{34}-V_{12})=h^2 \bullet (U_{12}+V_{12}-R\bullet U_{34}-R\bullet V_{34}) \quad (58)$$

$$f=h\bullet((U_{12}+V_{12}-R\bullet U_{34}-R\bullet V_{34})/(R\bullet V_{34}-V_{12})^{1/2} \quad (59)$$

yielding equation 15

$$f=h\bullet((U_{12}-R\bullet U_{34})/(R\bullet V_{34}-V_{12})-1)^{1/2} \quad (60)$$

Operation of the Invention

Figure 9:
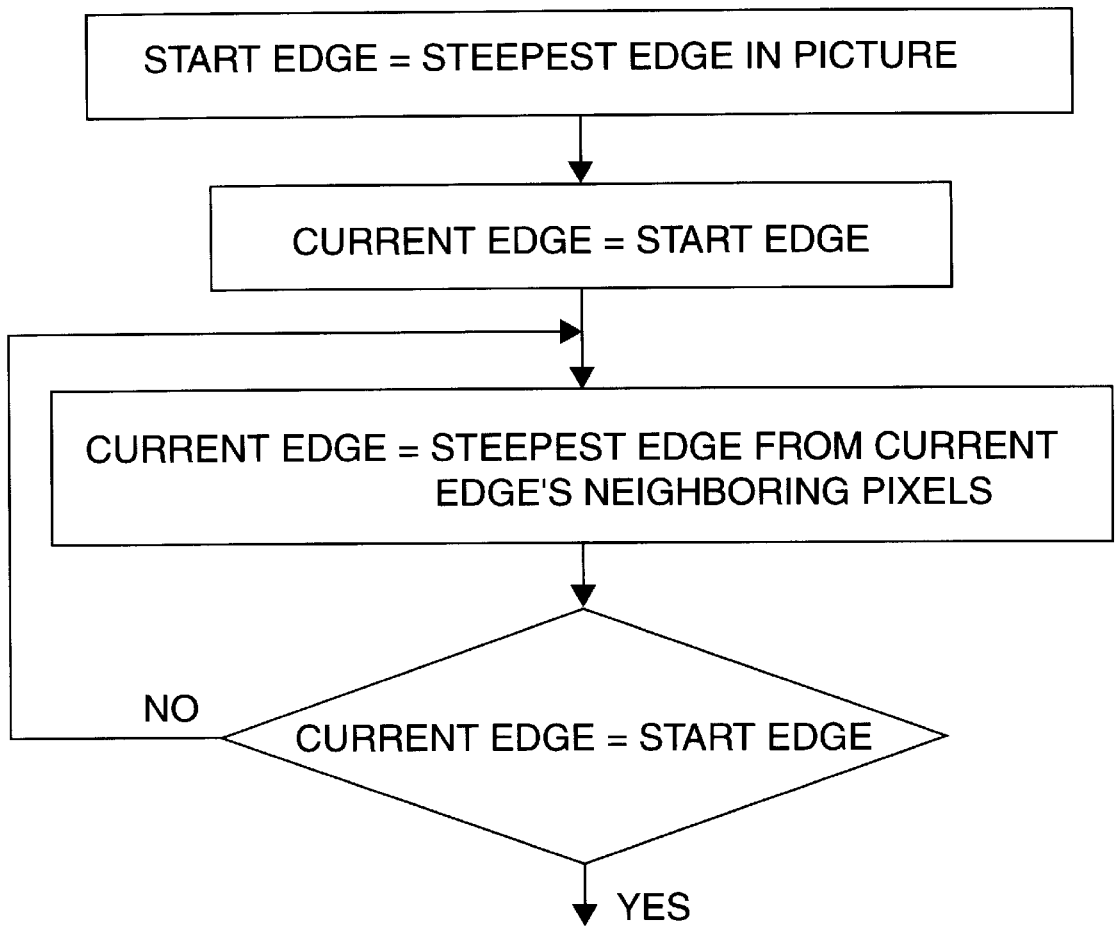
FIG. 9 is a flow chart showing a method of locating features of a target plate, according to the present invention.
Figure 22:
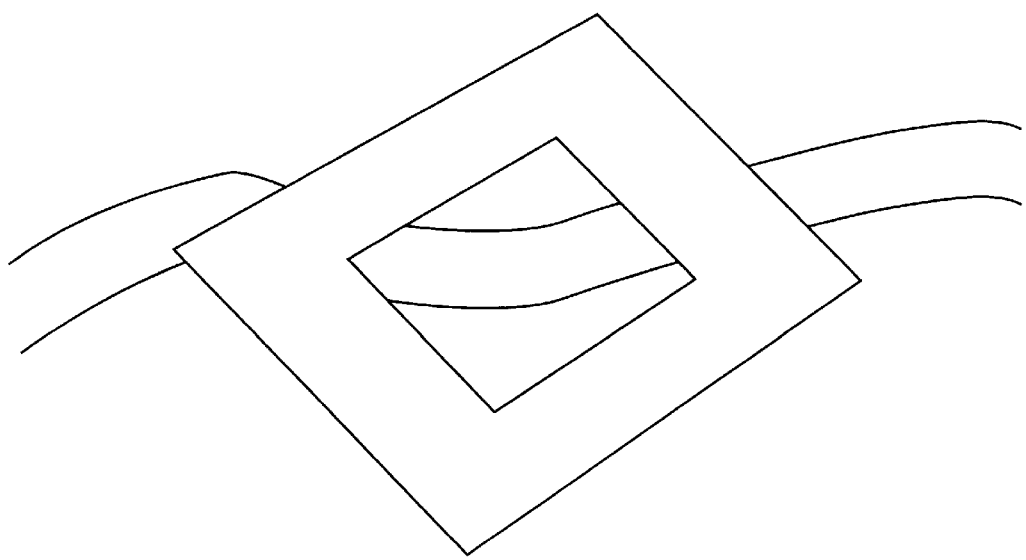
FIG. 22 is a perspective view of an alternate embodiment of a target object according to the present invention, in which the target object has an open area which may be positioned to overlie a wound.

Referring now to FIGS. 7 through 9, in addition to FIG. 1, a still or video picture of a wound 34 is photographed along with an adjacent target plate 36 containing a control rectangle 37. Preferably, the camera focal length and distance from the wound are adjusted to maximize the size of the wound image in the camera focal plane, while stil maintaining the control rectangle within the field of view of the camera.

Also, the photograph of the wound preferably is time and date stamped, and preceded or succeeded with still or video photographic frames showing the patient's face, identification number, etc., to provide positive documentary evidence of the wound measurement procedure.

After a photograph of a wound has been taken as shown in FIG. 1 and described above, the photograph is scanned, digitized and input to computer 44. Then, as shown in FIGS. 7 and 8, an operator 45 selects a wound image 32W, such as the wound image 32W shown in FIG. 10, for display on monitor 47. As shown in FIGS. 3–6 and described above, a pair of intersecting lines forming a first corner of image 32R of target plate 37 in digitized image 43 is located visually on the screen of monitor 47, whereupon a cursor is placed on the corner by an operator, and the X-Y coordinates of the first corner in the monitor frame of reference entered into computer memory by the operator. These coordinates locate the origin of the X-Y coordinate system of the control plane.

In an exactly similar manner, the coordinates of the remaining three corners of control rectangle image 32R are entered into computer 44. Then, the coordinates of the control rectangle in the picture plane are transformed into the "real world" coordinates of the rectangle in the control plane, by the coordinate transformation indicated in equations 6, 7, 18, 19, 23, 24, thus forming a normal, perpendicular view of the control rectangle. With the entry into computer 45 of the known lengths of the sides of control rectangle 37, the image of the rectangle in the control plane will be of known scale.

Transforming a quadrilateral image 32R of target plate rectangle 37, such as image 32R in FIG. 11 into a "real world" rectangle 37N, as shown in FIG. 12 of known dimensions in the control plane entails derivation of rotation angle $\theta$, camera focal length f, distance from the camera to the control plane, pitch angle $\alpha$, and yaw angle $\phi$, according to equations (5), (15), (16), (17) and (22). These four parameters 34 are then stored in memory of computer 44, and used to calculate the "real world" shape 34N and dimensions of a wound 34 from the coordinates of its oblique image 32W in the picture plane. To perform this operation, operator 45 moves a cursor onto the desired wound features (FIG. 12), and enters the monitor or picture plane coordinates of the features into the computer, whereupon equations (23) and (24) are used to calculate the "real world" coordinates of the features. Thus, by tracing the perimeter of the wound image with the computer monitor cursor, a normal view of the wound perimeter may be calculated and displayed according to the method of the present invention, as shown in FIG. 12. Also, since the scale of the normal view of a wound, such as the wound shown in FIG. 12, is known, the outline or perimeter of the normal wound image may be used to calculate the exact area of the wound, using conventional area calculation algorithms such as the polygon algorithm described below.

Area of polygon $P_1, P_2, \cdots O_n$

Area=½($x_1 \cdot y_2 + x_2 \cdot y_3 + \cdots x_{n-1} \cdot y_n + x_n \cdot y_1 - y_1 \cdot x_2 - y_2 \cdot x_3 - \cdots - y_{n-1} x_n - y_n \cdot x_1$)

In the preferred embodiment, the novel method of the present invention utilizes a contrast edge tracking algorithm to automatically locate the corners of target plate rectangle 37 in the picture plane. This algorithm, depicted in FIG. 9 functions as follows:

1. Locate the steepest edge in entire picture and call this location start edge.
2. Set the current edge to start edge.
3. From the current edge's neighboring locations find the steepest edge and set the current edge to that location.
4. Repeat No. 3 until current edge equals start edge.

Figure 10:
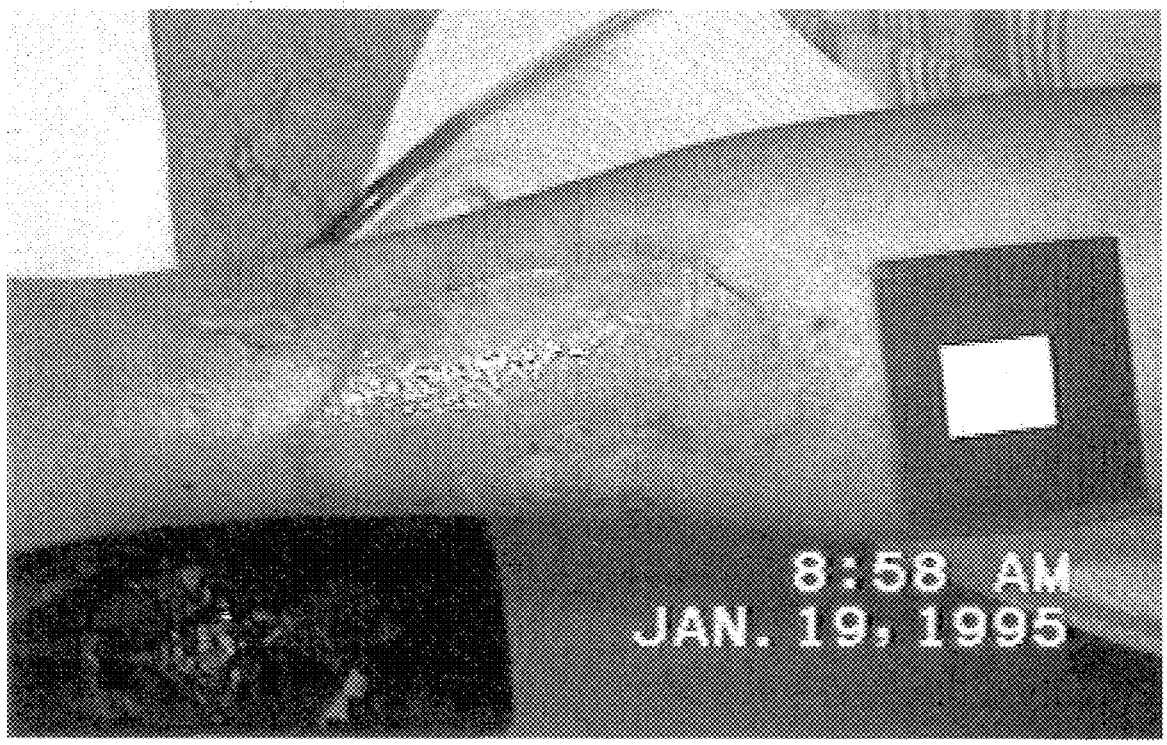
FIG. 10 is a perspective view of a target plate according to the present invention, showing the target plate placed adjacent to an ulcer on the right leg of a patient.
Figure 13:
FIG. 13 is a perspective view similar to that of FIG. 10, but taken at a later date.
Figure 16:
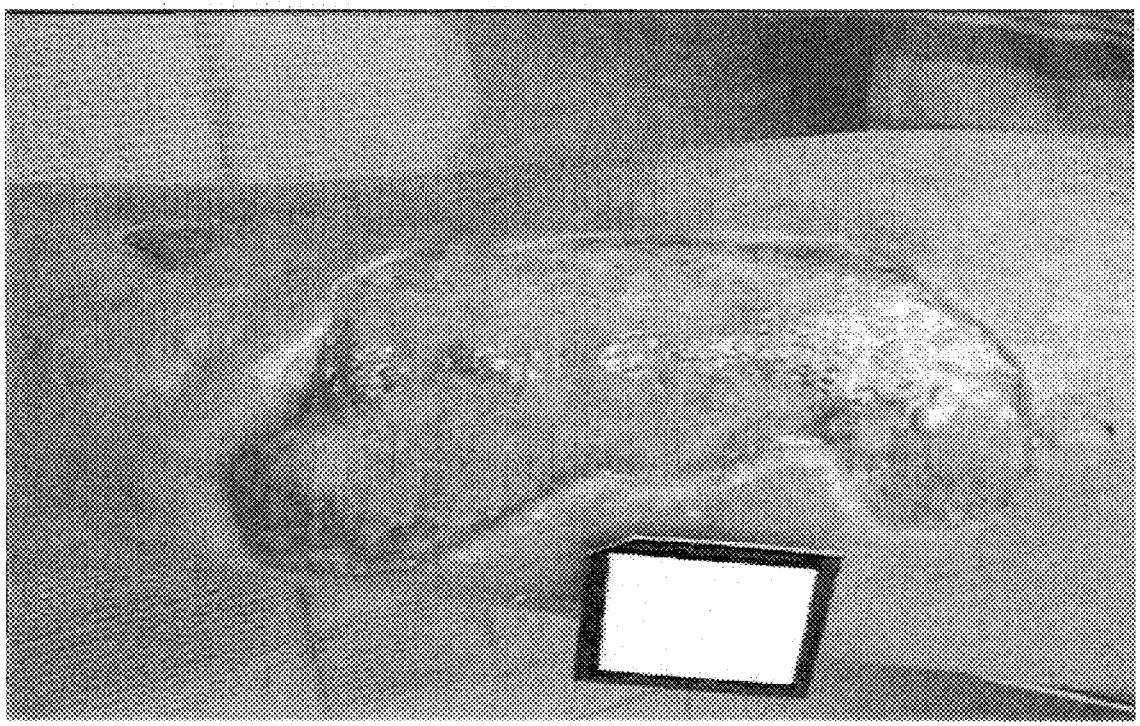
FIG. 16 is a perspective view similar to that of FIG. 13, but taken at a still later date.
Figure 19:
FIG. 19 is a perspective view similar to that of FIG. 16, but taken at an even later date.

FIGS. 13, 16 and 19 show photographic images 32 of different wounds, analogous to FIG. 10.

FIGS. 14, 17, and 20 show digitized oblique planar images of the wounds of FIGS. 13, 16 and 19, respectively, analogous to FIG. 11.

FIGS. 15, 18, and 21 show digitized planar images similar to those of FIGS. 14, 17, and 20, but with the images re-oriented to normal views, similar to that of FIG. 12.

Example of 2D Measurement From A Picture

Given

Figures 24A, 24B:
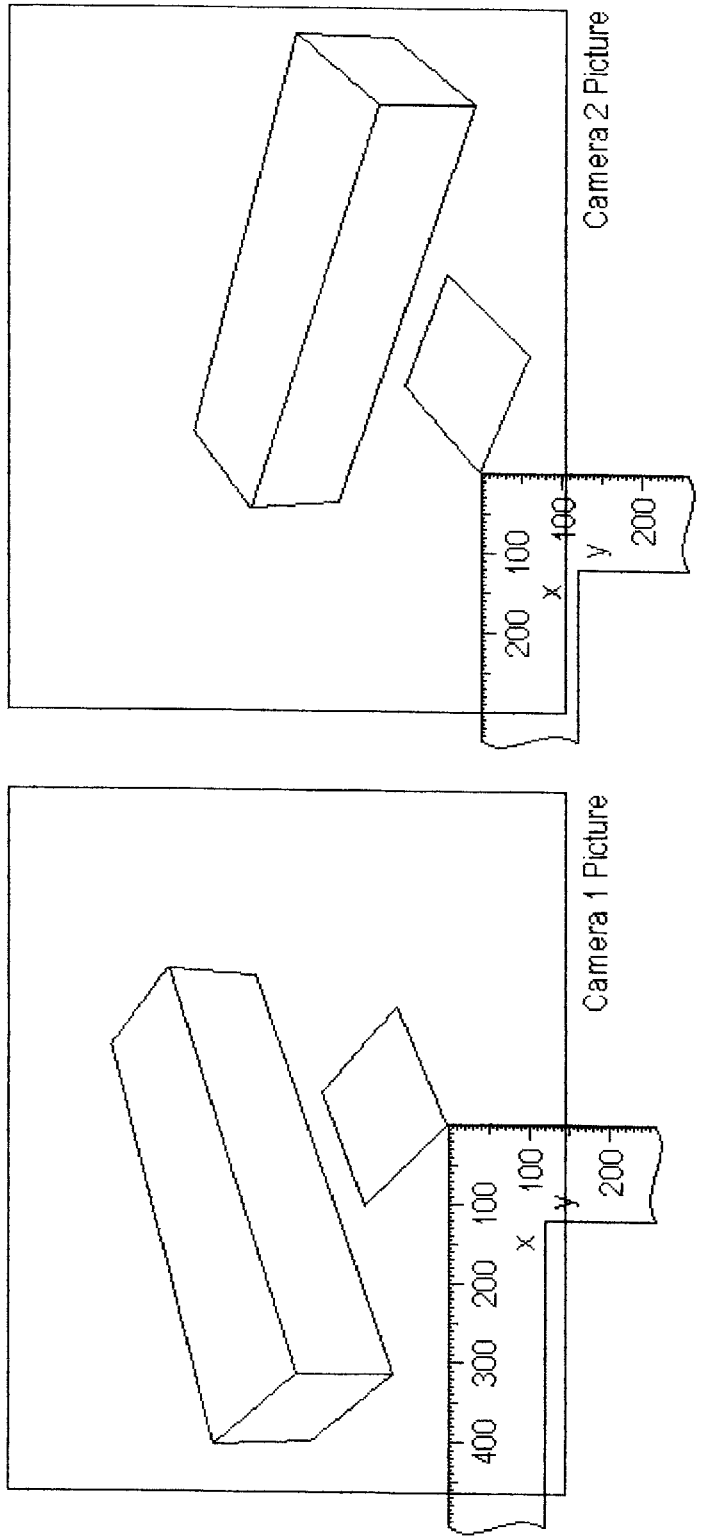
FIG. 24A is a planar camera image showing the relationships between dimensions of the control rectangle and box of FIG. 23.
FIG. 24B is a view similar to that of FIG. 24A, but showing a different camera image.

A digital picture of resolution 580×480 (See FIG. 24A). The picture coordinates (x, y) of the four corners of a 1 inch square as it appears in the picture.
1. 528.657, 173.343
2. 464.753, 145.661
3. 421.317, 192.106
4. 483.920, 218.080

Calculate the Line Equation Coefficients $$\text{Using the general equation of a line } A \cdot x + B \cdot y + C = 0 \quad (61)$$

$$\text{where } A = Y_1 - Y_2, B = x_2 - x_1, C = x_1 \cdot y_2 - y_1 \cdot x_2 \quad (62)$$

determine the four lines that form the quadrilateral.

1-2. A=173.343−145.681=27.662, B=464.753−528.657=−63.904, C=528.657•146.681−173.343•464.753=−3546.399

2-3. A=−46.425, B=−43.436, C=27903.958

3-4. A=−25.974, B=62.603, C=1083.124

4-1. A=44.737, B=44.737, C=31405.374

Figure 26D:
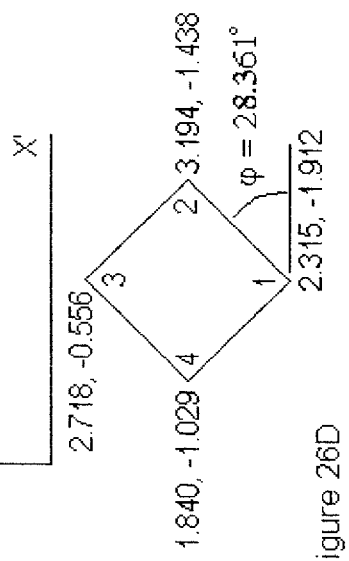
Figure 26C:
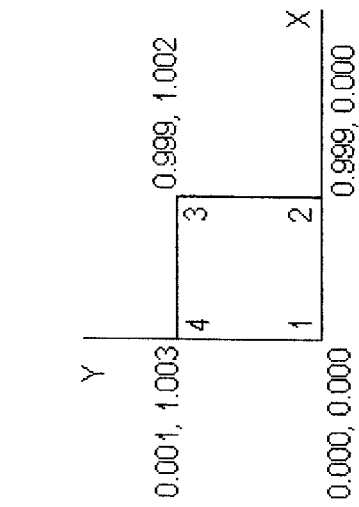
Figure 26A:
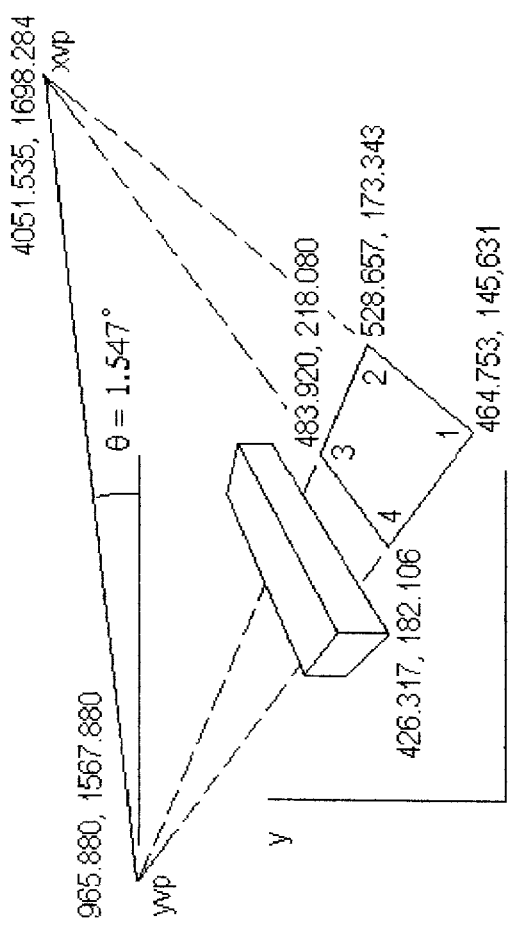

Calculate the Vanishing Points' Coordinates (See FIG. 26A)

The vanishing points are determined by the intersection of line 1-2 with line 3-4 and the intersection of line 2-3 with line 4-1 using equations 1 and 2:

$$x = (B_2 \cdot C_1 - B_1 \cdot C_2)/(B_1 \cdot A_2 - B_2 \cdot A_1) \quad (63)$$

$$y = (C_1 + A_1 \cdot x)/B_1 \quad (64)$$

Intersect line 1-2 and line 3-4

$x = (62.603 \cdot -3546.399 - [-63.904] \cdot -1083.124)/(-63.904 \cdot -25.974 - 82.603 \cdot 27.882) = 4051.535$ $y = -(-3546.399 + 27.662 \cdot 4051.535)/-63.904 = 1698.284$ Interest line 2-3 and line 1-4

$x = (44.737 \cdot 27903.958 - [-43.436] \cdot -31405.374)/(-43.436 \cdot 44.737 - 44.737 \cdot -46.425) = -885.880$ $y = -(27903.958 + [-46.425] \cdot -665.880)/-43.436 = 1587.880$ Reorder the Points (See FIG. 26A)

The control rectangle corner points must be ordered such that the first point is the point that forms the largest triangle with the vanishing points and the other points are ordered counter-clockwise around the rectangle. By visual inspection the correct order is 1. 464.753, 145.681
2. 528.657, 173.343
3. 483.920, 218.080
4. 421.317, 192.106

Calculate the Rotation Angle (See FIG. 26A)

Define the x-axis vanishing point as the intersection of line 1-2 and line 3-4 and define the y-axis vanishing point as the intersection of line 2-3 and line 4-1.

Intersection of line 1-2 and line 3-4 (x-axis vanishing point)

$x_{xvp} = 4051.535$ $y_{xvp} = 1698.284$

Intersection of line 2-3 and line 4-1 (y-axis vanishing point)

$x_{yvp} = -885.880$ $y_{yvp} = 1567.880$

The rotation angle equals the angle between the x-axis and the vector running from the y-axis vanishing point ($y_{vp}$) to the x-axis vanishing point ($x_{vp}$).

Using equation 5:

$$\theta = \text{Tan}^{-1}((y_{xvp} - y_{yvp})/(x_{xvp} - x_{yvp}))$$

$$\theta = \text{Tan}^{-1}((1698.254 - 1567.880)/4051.535 - [-885.880]))$$

$$\theta = 0.027 \text{ radians} = 1.547 \text{ degrees}$$

Figure 26B:
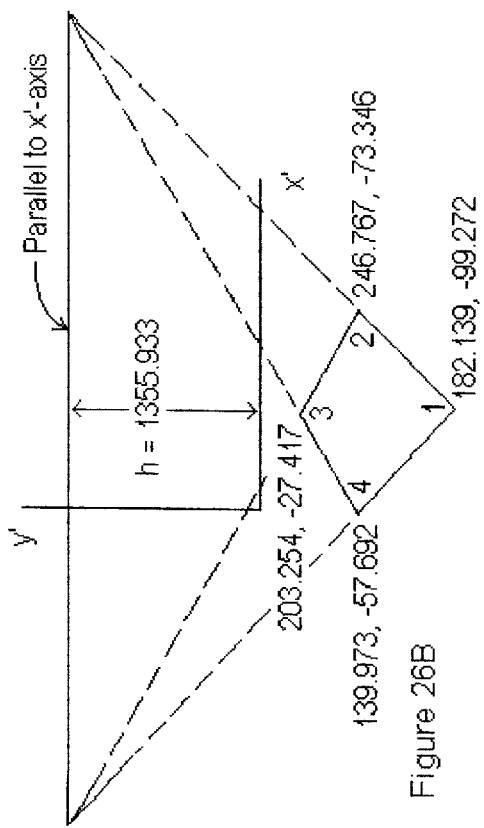

Calculate the Distance from the Focal Center to the Horizon Line, h (See FIG. 26B)

Using equation 8:

$$h = y'_{xvp}$$

Using equation 7:

$$y'_{xvp} = (y_{xvp} - y_0) \cdot \cos\theta - (x_{xvp} - x_0) \cdot \sin\theta$$

$x_0, y_0$ = center of the picture = 560/2, 480/2 = 280,240

$$h = (1698.284 - 240) \cdot \cos(0.027) - (4051.535 - 280) \cdot \sin(0.027) = 1355.933$$

Calculate the Focal Length, f
Using equations 6 and 7:

$$x' = (x - x_0) \cdot \cos\theta + (y - y_0) \cdot \sin\theta$$

$$y' = (y - y_0) \cdot \cos\theta - (x - x_0) \cdot \sin\theta$$

$$x' = (x - 280) \cdot \cos(0.027) + (y - 240) \cdot \sin(0.027)$$

$$y' = (y - 240) \cdot \cos(0.027) - (x - 280) \cdot \sin(0.027)$$

$$x'_1 = (464.753 - 280) \cdot -0.39862 + (145.651 - 240) \cdot -0.91711$$

$$y'_1 = (145.681 - 240) \cdot -0.39862 - (145.681 - 280) \cdot (0.91711$$

$$x'_1 = 182.139$$

$$y'_1 = -99.272$$

$$x'_2 = (528.657 - 280) \cdot -0.39862 + (173.343 - 240) \cdot -0.91711$$

$$y'_2 = (173.343 - 240) \cdot -0.39862 - (528.657 - 280) \cdot -091711$$

$$x'_2 = 246.767$$

$$y'_2 = -73.346$$

$$x'_3 = (483.920 - 280) \cdot -039862 + (218.080 - 240) \cdot -0.91711$$

$$y'_3 = (218.080 - 240) \cdot -039862 - (483.920 - 280) \cdot -0.91711$$

$$x'_3 = 203.254$$

$$y'_3 = -27.417$$

$$x'_4 = (421.317 - 280) \cdot -0.39862 + (192.106 - 240) \cdot -0.91711$$

$$y'_4 = (192.106 - 240) \cdot -0.39862 - (421.317 - 280) \cdot -091711$$

$$x'_4 = 139.973$$

$$y'_4 = -51.692$$

Using equation 10:

$$U_{13} = (x'_1/(-y'_1) - x'_3/(h - y'_3))^2$$

$$U_{13} = (182.139/(1355.933 - [-199.272]) - 203.254/(1355.933 - [-27.417]))^2 = 0.00047$$

Using equation 11:

$$V_{13} = (y'_1/(h - y'_1) - y'_3/(h - y'_3))^2$$

$$V_{13} = (-99.272/(1355.933 - [-99.272]) - [-27.417]/(1355.933 - [-27.417]))^2 = 0.00234$$

Using equation 12:

$$U_{24} = (x'_2/(h - y'_2) - x'_4/(h - y'_4))^2$$

$$U_{24} = (246.757/(1355.933 - [-73.346]) - 139.973/(1355.933 - [-51.692]))^2 = 0.00536$$

Using equation 13:

$$V_{24} = (y'_2) - y'_4/(h - y'_4))^2$$

$$V_{24} = (-73.346/(1355.933 - [-73.346]) - [-51.692]/(1355.933 - [-51.692]))^2 = 0.00021$$

$D_{13}$, $D_{24}$ is the real-world length of the diagonals of the control rectangle = 1.414.

therefore, using equation 14, $R = D_{13}^2/D_{24}^2 = 1$
Using equation 15 the focal length is then $$f = h \cdot ((U_{13} - R \cdot U_{24})/(R \cdot V_{24} - V_{13}) - 1)^{1/2}$$

$$f = 1355.933 \cdot ((0.00047 - 1 \cdot 0.00536)/(1 \cdot 0.00021 - 0.00234)1)^{1/2} = 1543.487$$

Calculate the Distance from the Camera to the Control Plane, $Z_0$
Using equation 16:

$$Z_0 = ((f \cdot h \cdot D_{13})^2/(H^2 \cdot h^2 \cdot U_{13} + H^4 \cdot V_{13}))^{1/2}$$

where $H = (h^2 + f^2)^{1/2}$ $$H = (1355.933^2 + 1543.487^2)^{1/2} = 2054.484$$

$$Z_0 = ((1543.487 \cdot 1355.933 \cdot 1.414)^2/(2054.484^2 \cdot 1355.933^{1/2} \cdot 0.00047 + 2054.484^4 \cdot 0.00234))^{1/2}$$

$$Z_0 = 13.898$$

Calculate the Pitch Angle, $\alpha$
The pitch angle is the angle between the picture plane and the control plane and is determined by using equation 17:

$$\alpha = \tan^{-1}(f/h)$$

$$\alpha = \tan^{-1}(1543.487/1355.933)$$

$$\alpha = 0.850 \text{ radians} = 48.701 \text{ degrees}$$

Converting x', y' Coordinates to X', Y' Coordinates
Using equation 18:

$$X' = M \cdot x'/(h - y')$$

where $M = Z_0 \cdot H/f$ $$M = 13.698 \cdot 2054.484/1543.487 = 18.499$$

$$X' = 18.499 \cdot x'/(1355.933 - y')$$

Using equation 19:

$$Y' = N \cdot y'/(h - y')$$

where $N = Z_0 \cdot H^2/(f \cdot h)$ $$N = 13.898 \cdot 2054.484^2/(1543.487 \cdot 1355.933) = 28.030$$

$$Y' = 28.030 \cdot y'/(1355.933 - y')$$

Calculate the Yaw Angle $\phi$ (See FIG. 26D)
Using equations 18 and 19, with appropriate substitutions:

$$X' = 18.499 \cdot x'/(1355.933 - y')$$

$$Y' = 28.030 \cdot y'/(1355.933 - y')$$

$$X'_1 = 18.499 \cdot 182.139/(1355.933 - [-99.272]) = 2.315$$

$$Y'_1 = 28.030 \cdot -99.272/(1355.933 - [-99.272]) = -1.912$$

$$X'_2 = 18.499 \cdot 246.767/(1355.933 - [-73.346]) = 3.194$$

$Y'_2=28.030\cdot-73.346/(1355.933-[-73.346])=-1.438$

Using equation 22:

$\phi=\text{Tan}^{-1}((Y'_2-Y'_1)/(X'_2-X'_1))$ $\phi=\text{Tan}^{-1}((-1.438-[-1.912])/3.194-2.315))=0.495$ radians=28.361 degrees Converting X', Y' Coordinates to X, Y Coordinates $X=(X'-X'_1)\cdot\cos\phi+(Y'-Y'_1)\cdot\sin\phi$ $Y=(Y'-Y'_1)\cdot\cos\phi-(X'-X'_1)\cdot\sin\phi$ $X=(X'-2.315)\cdot\cos(0.495)+(Y'-[-1.912])\cdot\sin(0.495)$ $Y=(Y'-[-1.912])\cdot\cos(0.495)-(X'-2.315)\cdot\sin(0.495)$ Calculate the Camera's Position $X_0, Y_0$:

$X'_0=0$

Using equation 26:

$Y'_0=-f\cdot Z_0/h=1543.487\cdot 13.898/1355.933=-15.820$ $X_0=(0-2.315\cdot\cos(0.495)+(-15.820-[-1.912])\cdot\sin(0.495)=-8.644$ $Y_0=(-15.820-[-1.912])\cdot\cos(0.495)-(0-2.315)\cdot\sin(0.495)=-13.338$ Converting x, y Coordinates to X, Y Coordinates (see FIG. 26)

Now that we have the camera's position and orientation we can calculate the locations of any point in the picture as projected onto the control plane relative to the control rectangle. For an example we will calculate the locations of the control rectangle's corners.

Using equations 6 and 7 with appropriate substitutions:

$x'=(x-280)\cdot\cos(0.027)+(y-240)\cdot\sin(0.027)$ $y'=(y-240)\cdot\cos(0.027)-(x-280)\cdot\sin(0.027)$ then, using equations 18 and 19 with appropriate substitutions:

$X'=18.499\cdot x'/(1355.933-y')$ $Y'=28.030\cdot y'/(1355.933-y')$ then, using equations 23 and 24 with appropriate substitutions:

$X=(X'-2.315)\cdot\cos(0.495)+(Y'--1.912)\cdot\sin(0.495)$ $Y=(Y'--1.912)\cdot\cos(0.495)-(X'-2.315)\cdot\sin(0.495)$ $x'_1=(464.753-280)\cdot\cos(0.027)+(145.681-240)\cdot\sin(0.027)=182.139$ $y'_1=(145.681-240)\cdot\cos(0.027)-(484.753-280)\cdot\sin(0.027)=-99.272$ $X'_1=18.499\cdot 182.139/(1355.933-[-99.272])=2.315$ $Y'_1=28.030\cdot-99.272/(1355.933-[-99.272])=-1.912$ $X_1=(2.315-2.315)\cdot\cos(0.495)+(-1.912-[-1.912])\cdot\sin(0.495)=0$ $Y_1=(-1.912-[-1.912])\cdot\cos(0.495)-(2.315-2.315)\cdot\sin(0.495)=0$ $x'_2=(528.657-280)\cdot\cos(0.027)+(173.343-240)\cdot\sin(0.027)=246.767$ $y'_2=(173.343-240)\cdot\cos(0.027)-(528.657-280)\cdot\sin(0.027)=-73.346$ $X'_2=18.499\cdot 246.767/(1355.933-[-73.346])=3.194$ $Y'_2=28.030\cdot-73.346/(1355.933-[-73.346])=-1.435$ $X_2=(3.194-2.315)\cdot\cos(0.495)+(-1.438-[-1.912])\cdot\sin(0.495)=0.999$ $Y_2=(-1.438--1.912)\cdot\cos(0.495)-(-1.912-2.315)\cdot\sin(0.495)=0.000$ $x'_3=(483.920-280)\cdot\cos(0.027)+(216.080-240)\cdot\sin(0.027)=203.254$ $y'_3=(218.080-240)\cdot\cos(0.027)-(483.920-280)\cdot\sin(0.027)=-27.417$ $X'_3=18.499\cdot 203.254/(1355.933-[-27.417])=\mathbf{2.718}$ $Y'_3=28.030\cdot-27.417/(1355.933-[-27.417])=-0.556$ $X_3=(2.718-2.315)\cdot\cos(0.495)+(-0.556-[-1.912])\cdot\sin(0.495)=-0.999$ $Y_3=(-0.558-[-1.912])\cdot\cos(0.495)-(2.718-2.315)\cdot\sin(0.495)=1.002$ $x'_4=(421.317-280)\cdot\cos(0.027)+(192.106-240)\cdot\sin(0.027)=\mathbf{139.973}$ $y'_4=(192.106-240)\cdot\cos(0.027)-(421.317-280)\cdot\sin(0.027)=-\mathbf{51.692}$ $X'_4=18.499\cdot 139.973/(1355.933-[-51.692])=1.840$ $Y'_4=28.030\cdot-51.692/(1355.933-[-51.692])=-\mathbf{1.029}$ $X_4=(1.840-2.315)\cdot\cos(0.495)+(-1.029-[-1.912])\cdot\sin(0.495)=0.001$ $Y_4=(-1.029-[-1.912])\cdot\cos(0.495)-(1.840-2.315)\cdot\sin(0.495)=1.003$ $X_1, Y_1=0.000, 0.000$ $X_2, Y_2=0.999, 0.000$ $X_3, Y_3=0.999, 1.002$ $X_4, Y_4=0.001, 1.003$ The expected values for the above four coordinates are $X_1, Y_1=0, 0$ $X_2, Y_2=1, 0$ $X_3, Y_3=1, 1$ $X_4, Y_4=0, 1$ The differences between the expected result and the actual result is due to the inaccuracy in determining the picture coordinates of the control rectangle corners, assumptions made about the location of the focal center, and image distortions.

Having obtained equations for transforming oblique image coordinates of a target rectangle to a computer image having the same size and shape as the actual target rectangle, in the manner described above, the same equations may be used to transform an oblique wound image into a normal-view image depicting the actual size and shape of the wound.

Example of 3D Measurement From Two Pictures

Given:

Two digital pictures of the same subject (a control rectangle and a box) the box simulating a three-dimensional object such as a wound. (See FIGS. 24A and 24B)

Calculate the Camera's Position and Orientation (See 2D Example)

The first camera's coordinates $(X_{c1}, Y_{c1}, Z_{c1})$ are $-8.644, -13.338, 13.898$ The second camera's coordinates $(X_{c2}, Y_{c2}, Z_{c2})$ are $5.797, -7.466, 9.423$ Calculate the Projection Points The picture coordinates (x, y) of a corner of the box as it appears in the first picture and the real-world coordinates (X, Y, O) of the corner projected onto the control rectangle plane are:

| (x, y) | (X, Y, O) |
|---|---|
| 147, 302 | -2.109, 4.929, 0 |

The picture coordinates (x, y) of the same corner of the box as it appears in the second picture and the real-world coordinates (X, Y, O) of the corner projected onto the control rectangle plane are:

| (x, y) | (X, Y, O) |
|---|---|
| 286, 390 | -4.061, 5.533, 0 |

Calculate the X, Y, Z Coordinates

The projection line for a point in a picture passes through the camera focal point and through that point's projection onto the control plane. If a point in one picture matches a point in another picture taken from a different perspective, then the intersection of their projection lines occurs at the 3D coordinates of the object.

$$A_1 = Z_{c1} \cdot (Y_{c2} - Y_{c2}) - Z_{c2} \cdot (Y_{c1} - Y_1) \quad (65)$$

$A_1 = 13.898 \cdot (-7.466 - 5.580) - 9.423 \cdot (-13.338 - 4.911) = -8.530$ $$B_1 = Z_{c1} \cdot (Y_2 - Y_1) \quad (66)$$

$B_2 = 13.898 \cdot (5.580 - 4.911) = 8.394$ $$C_1 = Z_{c2} \cdot (X_{c1} - X_1) - Z_{c1} \cdot (X_{c2} - X_2) \quad (67)$$

$C_1 = 9.423 \cdot (-8.644 - [-2.124]) - 13.898 \cdot (5.797 - -4.035) = -198.586$ $$D_1 = -Z_{c1} \cdot (X_2 - X_1) \quad (68)$$

$D_1 = -13.698 \cdot (-4.035 - [-2.124]) = 26.129$ $$E_1 = (Y_{c1} - Y_1) \cdot (X_{c2} - X_2) - (X_{c1} - X_1) \cdot (Y_{c2} - Y_2) \quad (69)$$

$E_1 = (-13.338 - 4.911) \cdot (5.797 - [-4.035]) - (-8.644 - [-2.124]) \cdot (-7.466 - 5.680) = -265.025$ $$F_1 = (Y_{c1} - Y_1) \cdot (X_2 - X_1) - (X_{c1} - X_1) \cdot (Y_2 - Y_1) \quad (70)$$

$F_1 = (-13.338 - 4.911) \cdot (-4.035 - [-2.124]) - (-8.644 - [-2.124]) \cdot (5.680 - 4.911) = 39.604$ $$t_1 = -A_1 \cdot B_1 - C_1 \cdot D_1 \cdot E_1 \cdot F_1 \quad (71)$$

$t_1 = 8.530 \cdot 8.394 - [-198.586] \cdot 26.129 - [-265.025] \cdot 39.604 = 0.145$ $$A_2 = -A_1 \quad (72)$$

$A_2 = 8.530$ $$B_2 = -Z_{c2} \cdot (Y_2 - Y_1) \quad (73)$$

$B_2 = -9.423 \cdot (5.580 - 4.911) = -5.891$ $$C_2 = C_1 \quad (74)$$

$C_2 = 198.588$ $$D_2 = Z_{c2} \cdot (X_2 - X_1) \quad (75)$$

$D_2 = 9.423 \cdot (-4.035 - [-2.124]) = -18.394$ $$E_2 = -E_1 \quad (76)$$

$E_2 = 265.025$ $$F_2 = (X_{02} - X_2) \cdot (Y_2 - Y_1 - (Y_{02} - Y_2) \cdot (X_2 - X_1) \quad (77)$$

$F_2 = (5.797 - [-4.035]) \cdot (5.580 - 4.911) - (-7.466 - 5.580) \cdot (-4.035 - [-2.124]) = -19.420$ $$t_2 = -A_2 \cdot B_2 - C_2 \cdot D_2 - E_2 \cdot F_2 \quad (78)$$

$t_2 = -8.530 \cdot -5.691 - 198.586 \cdot -18.394 - 285.025 \cdot -19.420 = 0.081$ $$X = (X_1 + X_2 + t_1 \cdot (X_{c2} - X_2) + t_2 \cdot (X_{c1} - X_1))/2 \quad (79)$$

$X = (-2.124 + -4.035 + 0.145 \cdot (5.797 - [-4.036]) + 0.081 \cdot (-8.644 - [-2.124]))/2 = -2.635$ $$Y = (Y_1 + Y_2 + t_1 \cdot (Y_{c2} - Y_2) + t_2 \cdot (Y_{c1} - Y_1))/2 \quad (80)$$

$Y = (4.911 + 5.580 + 0.145 \cdot (-7.466 - 5.580) + 0.081 \cdot (-13.338 - 4.911))/2 = 3.549$ $$Z = (t_1 \cdot Z_{c2} + t_2 \cdot Z_{c1})/2 \quad (81)$$

$Z = (0.145 \cdot 9.423 + 0.081 \cdot 13.895)/2 = 1.246$

What is claimed is:

1. A method for remotely determining the normal view shape of a region of biological tissue such as a wound comprising;
   a. positioning a target object having a target plane containing known contrasting visual features and dimensions so as to locate said target plane proximate a plane tangent to a wound,
   b. forming an optical image of said target object and said wound using an optical imaging system that has an optical axis which may be inclined at an arbitrary oblique angle to a normal to said tangent plane of said wound and said target plane,
   c. determining a coordinate transformation that maps an oblique image of said target object into normal view thereof,
   d. mapping by said coordinate transformation said image of said target object into a normal image thereof, and
   e. mapping by said coordinate transformation said wound image, thereby obtaining a normal image of said wound.

2. The method of claim 1 further including the step of determining the size of selected features of said wound.

3. The method of claim 2 wherein said size determination step includes measuring the length of features of said normal image of said target object, dividing the measured length by the real world length of the corresponding feature of the actual target object to obtain a ratio k, and multiplying the length of selected wound features in said transformed image by k.

4. The method of claim 1 wherein said target object is further defined as having thereon at least one, first optically imageable pair of intersecting lines.

5. The method of claim 4 wherein said first pair of intersecting line is further defined as defining a first corner of a polygon.

6. The method of claim 5 wherein said target object is further defined as having thereon a second pair of optically imageable intersecting lines, said second pair of intersecting lines defining a second corner of said polygon.

7. The method of claim 6 wherein said polygon is further defined as being a quadrilateral.

8. The method of claim 7 wherein said quadrilateral is further defined as being a rectangle.

9. The method of claim 4 wherein said first pair of optically imageable lines on said target object is further defined as defining on one side thereof an area of one color and on the opposite side thereof an area of a contrasting color.

10. The method of claim 4 wherein said target object is further defined as having thereon a transparent region.

11. The method of claim 4 wherein said target object is further defined as having through the thickness dimension thereof a perforation.

12. A method for optically assessing characteristics of a wound comprising:
   a. positioning a target object comprising a thin sheet having formed thereon optically contrasting fratures proximate a plane tangent to a wound,
   b. forming an optical image of said target object and said wound using an optical imaging system that has an optical axis which may be inclined at an oblique angle to a normal to said plane tangent to said wound and said target object,
   c. determining a coordinate transformation that maps an oblique image of said target object into a normal view thereof,
   d. mapping by said coordinate transformation said image of said target object into a normal image thereof,
   e. mapping by said coordinate transformation said wound image, thereby obtaining a normal image of said wound, and
   f. observing features of said normal image of said wound.

13. The method of claim 12 wherein the plane of said target object is positioned approximately coplanar with a tangent plane to said wound.

14. The method of claim 13 wherein said optically contrasting features of target object are further defined as including a rectangular shape.

15. The method of claim 14 wherein said coordinate transformation is further defined as mapping a quadrilateral image of said rectangle into a rectangle with sides in the same ratio as said rectangular shape of said target object.

16. An apparatus for remotely assessing characteristics of a wound comprising:
   a. a target object having a plane containing quantifiable visual features for placement proximate a plane tangent to a wound,
   b. means for forming a composite image including images of said target object and said wound at an arbitrary oblique angle to said wound and said target object,
   c. means for performing a coordinate transformation that maps an oblique image of said target object into a normal view thereof, and
   d. means for mapping by said coordinate transformation said image and said wound image of said target object into normal images thereof.

17. The apparatus of claim 16 further including means for measuring selected features of said wound image.

18. The apparatus of claim 16 wherein said target object is further defined as having thereon at least one first optically imageable pair of intersecting lines.

19. The method of claim 1 wherein said contrasting visual features of said target object are further defined as comprising two pairs of parallel, mutually perpendicular lines.

20. The method of claim 19 wherein said determination of said coordinate transformation is further defined as including the step of calculating vanishing points, each defined by the intersection on an oblique image thereof of each pair of parallel lines.

21. The method of claim 14 wherein said determinor of said coordinate transformation is further defined as including the step of calculating vanishing points, each defined by the intersection of an oblique image of each of a pair of mutually perpendicular parallel lines defining said rectangular shape.

* * * * *